US010760131B2

(12) United States Patent
Woods et al.

(10) Patent No.: US 10,760,131 B2
(45) Date of Patent: Sep. 1, 2020

(54) METHODS OF DETECTING, DIAGNOSING, AND TREATING ATHEROSCLEROTIC PLAQUE RUPTURE

(71) Applicants: THE ADMINSTRATORS OF THE TULANE EDUCATIONAL FUND, New Orleans, LA (US); OCHSNER CLINIC FOUNDATION, New Orleans, LA (US)

(72) Inventors: Thomas Cooper Woods, New Orleans, LA (US); Hernan Antonio Bazan, New Orleans, LA (US)

( * ) Notice: Subject to any disclaimer, the term of this patent is extended or adjusted under 35 U.S.C. 154(b) by 2 days.

(21) Appl. No.: 15/553,135

(22) PCT Filed: Feb. 23, 2016

(86) PCT No.: PCT/US2016/019184
§ 371 (c)(1),
(2) Date: Aug. 23, 2017

(87) PCT Pub. No.: WO2016/126713
PCT Pub. Date: Aug. 11, 2016

(65) Prior Publication Data
US 2018/0249359 A1 Aug. 30, 2018

Related U.S. Application Data

(60) Provisional application No. 62/120,071, filed on Feb. 24, 2015.

(51) Int. Cl.
*C12Q 1/6883* (2018.01)
*C12Q 1/6813* (2018.01)
*C12Q 1/6874* (2018.01)

(52) U.S. Cl.
CPC ......... *C12Q 1/6883* (2013.01); *C12Q 1/6813* (2013.01); *C12Q 1/6874* (2013.01); *C12Q 2600/112* (2013.01); *C12Q 2600/118* (2013.01); *C12Q 2600/158* (2013.01)

(58) Field of Classification Search
CPC ....... H04W 24/10; H04W 4/02; H04W 24/08; H04W 999/99; H04W 4/025; H04W 64/00
See application file for complete search history.

(56) References Cited

U.S. PATENT DOCUMENTS

| | | | |
|---|---|---|---|
| 6,582,908 B2 * | 6/2003 | Fodor | B01J 19/0046 435/288.3 |
| 2012/0165392 A1 | 6/2012 | Olson et al. | |
| 2014/0199329 A1 | 7/2014 | Wagner et al. | |
| 2016/0251720 A1 * | 9/2016 | Schulze | C12Q 1/6883 514/44 A |
| 2018/0214537 A1 * | 8/2018 | Mutzke | A61K 9/5169 |

FOREIGN PATENT DOCUMENTS

| WO | 2012050975 A2 | 4/2012 |
|---|---|---|
| WO | WO 2014160358 A1 | 10/2014 |

OTHER PUBLICATIONS

Bazan et al Journal of Vascular Surgery. Program book for the Vascular Annual Meeting, published May 20, 2014, p. 84S, Abstract PS212 (Year: 2014).*
Lightell et al. (Am Diabetes Assoc Scientific Sessions. Jun. 13, 2014, abstract 314-OR, available via URL: < discovery.northernlight.com/document.php?trans=view&docid=PE20140704000000670&vid=3326&datasource=PHE&context=proquest@northernlight.com> (Year: 2014).*
Cipollone et al Stroke. 2011. 42: 2556-2563 (Year: 2011).*
Bazan et al Atherosclerosis, Thrombosis, and Vascular Biology. 34(No. suppl 1, Abstract 123, 2014 (Year: 2014).*
U.S. Receiving Office, International Search Report and Written Opinion of the International Searching Authority in International Application No. PCT/US2016/019184, dated May 6, 2019, 10 pages.
Bazan, Hernan A., et al, "Recently Ruptured Carotid Plaques Have Increased Levels of Circular RNA-16, Which Negatively Regulates the Proproliferative and Antiapoptic MicroRNA-221: A NOvel Mediator of Carotid Plaque Rupture", May 2014, Abstract 123 in Arteriosclerosis, Thrombosis and Vascular Biology, vol. 34, single page.

* cited by examiner

*Primary Examiner* — Carla J Myers
(74) *Attorney, Agent, or Firm* — Schwabe, Williamson & Wyatt, P.C.

(57) ABSTRACT

Disclosed are methods of, and assay and kits for, detecting and diagnosing arterial plaque rupture using the expression of miR-222, mi-221 and circ284. Also disclosed are methods of treating arterial plaque rupture and methods of identifying agents for use thin the treatment of arterial plaque rupture.

8 Claims, 9 Drawing Sheets
Specification includes a Sequence Listing.

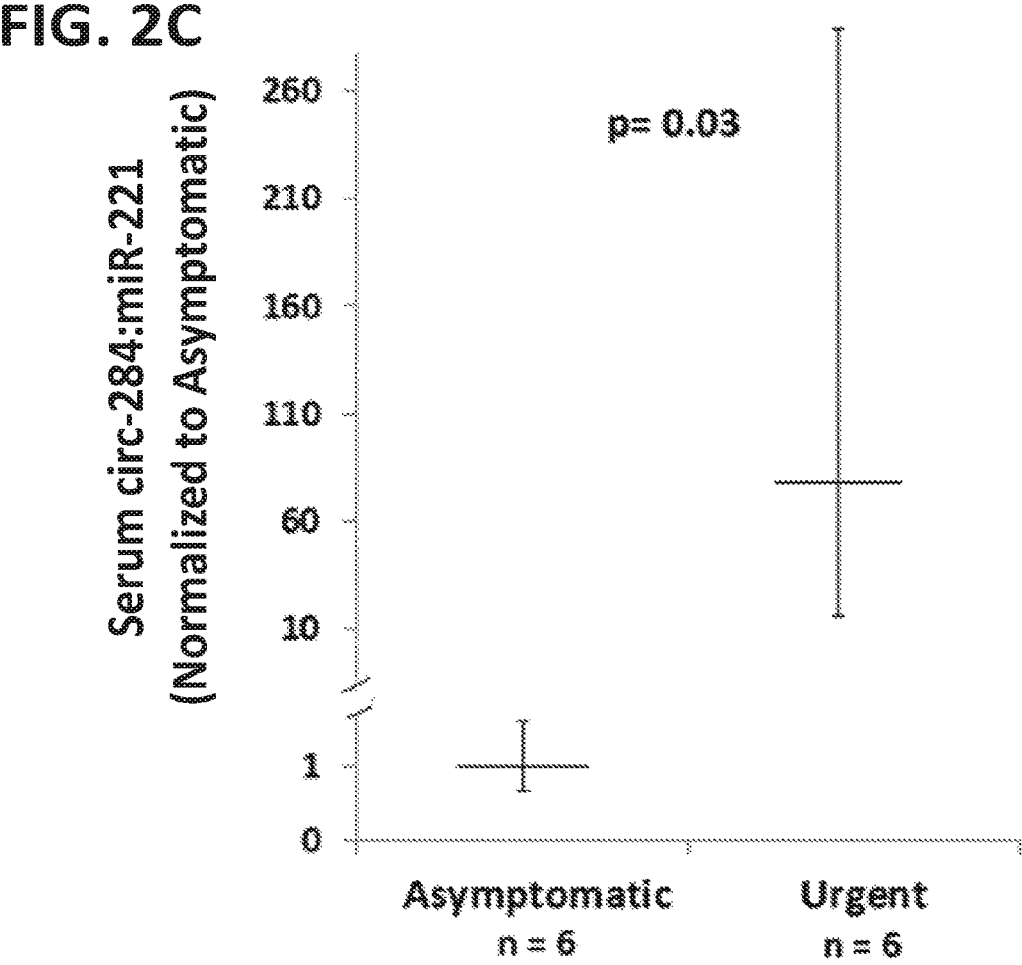

SEQUENCE LISTING

```
<160> NUMBER OF SEQ ID NOS: 4

<210> SEQ ID NO 1
<211> LENGTH: 88
<212> TYPE: RNA
<213> ORGANISM: homo sapiens

<400> SEQUENCE: 1
caccuugucc ucacggucca guuuucccag gaaucccuua gaugcuaaga ugggggauucc      60 uggaaauacu guucuugagg ucaugguu                                          88

<210> SEQ ID NO 2
<211> LENGTH: 110
<212> TYPE: RNA
<213> ORGANISM: Homo Sapiens

<400> SEQUENCE: 2
ugaacaucca ggucugggc augaaccugg cauacaaugu agauuucugu guucguuagg        60
```

```
caacagcuac auugucugcu ggguuucagg cuaccuggaa acauguucuc          110

<210> SEQ ID NO 3
<211> LENGTH: 110
<212> TYPE: RNA
<213> ORGANISM: Homo Sapiens

<400> SEQUENCE: 3
gcugcuggaa gguguaggua cccucaaugg cucaguagcc aguguagauc cugucuuucg  60
uaaucagcag cuacaucugg cuacuggguc ucgauggca ucuucuagcu           110

<210> SEQ ID NO 4
<211> LENGTH: 1100
<212> TYPE: RNA
<213> ORGANISM: homo sapiens

<400> SEQUENCE: 4
gguauggccu cacaagucuu ggucuaccca ccauauguuu aucaaacuca gucaagugcc  60
uuuuguagug ugaagaaacu caaaguagag ccaagcaguu guguauucca ggaaagaaac 120
uauccacgga ccuaugugaa ugguagaaac uuuggaaauu cucauccucc cacuaagggu 180
agugcuuuuc agacaaagau accauuuaau agaccucgag gacacaacuu uucauugcag 240
acaagugcug uuguuuugaa aaacacugca ggugcuacaa aggucauagc agcucaggca 300
cagcaagcuc acgugcaggc accucagauu ggggcguggc gaaacagauu gcauuccua  360 gaaggccccc agcgaugugg auugaagcgc aagagugagg aguuggauaa ucauagcagc 420
gcaaugcaga uugucgauga auuguccaua cuuccugcaa uguugcaaac caacauggga 480
aauccaguga caguugugac agcuaccaca ggaucaaaac agaauuguac cacuggagaa 540
ggugacuauc aguuaguaca gcaugaaguc uuaugcucca ugaaaaauac uuacgaaguc 600
cuugauuuuc uuggucgagg cacguuuggc caguaguua aaugcuggaa aagagggaca 660
aaugaaauug uagcaaucaa aauuuugaag aaucauccuu cuuaugcccg ucaaggucaa 720
auagaaguga gcauauuagc aaggcucagu acugaaaaug cugaugaaua uaacuuugua 780
cgagcuuaug aaugcuuuca gcaccguaac cauacuuguu uagucuuuga gaugcuggaa 840
caaaacuugu augacuuucu gaaacaaaau aaauuuaguc cccugccacu aaaagugauu 900
cggcccauuc uucaacaagu ggccacugca cugaaaaaau ugaaaagucu gguuuaauu  960 caugcugauc ucaagccaga gaauauuaug uugguggauc cuguucggca gccuuacagg 1020
guuaaaguaa uagacuuugg gucggccagu cauguaucaa agacuguuug uucaacauau 1080
cuacaaucuc gguacuacag                                         1100
```

METHODS OF DETECTING, DIAGNOSING, AND TREATING ATHEROSCLEROTIC PLAQUE RUPTURE

CROSS-REFERENCE TO RELATED APPLICATION

This application is a national phase entry under 35 U.S.C. § 371 of International Application No. PCT/US2016/019184, filed Feb. 23, 2016, entitled "METHODS OF DETECTING, DIAGNOSING, AND TREATING ATHEROSCLEROTIC PLAQUE RUPTURE," which designated, among the various States, the United States of America, and which claims the priority benefit of the earlier filing date of U.S. Provisional Application No. 62/120,071, filed Feb. 24, 2015, which is herein incorporated by reference in its entirety.

STATEMENT OF GOVERNMENT SUPPORT

This invention was made with government support under grant numbers P30GM103337 and U54GM104940 awarded by the National Institutes of Health. The government has certain rights in the invention.

TECHNICAL FIELD

This disclosure relates to assays and methods of detecting and diagnosing ruptured atherosclerotic plaques (such as in the carotid and coronary arteries) in order to prevent, anticipate, and better treat this and other complications of atherosclerosis, including carotid-related stroke and myocardial infarction. Specifically, newly discovered biomarkers, and novel methods for using them, are described.

BACKGROUND

Ischemic stroke or acute ischemic stroke (AIS) is typically defined as permanent brain injury secondary to disruption of blood flow. The incidence of AIS is approximately 700,000 per year, with about 61,000 deaths (see Adams et al. Emergency Medicine. Acute Ischemic Stroke: 1072). Although care of the subject with AIS begins with the public recognition and emergency medical system (EMS) instituting an expeditious transport, the formal evaluation and treatment of AIS occurs in the emergency department.

Carotid artery disease occurs when the carotid arteries, located in a person's neck, become narrowed. The carotid arteries are more likely to develop carotid artery disease as a person ages and has risk factors for atherosclerosis, including but not exclusive of hypercholesterolemia, hypertension, diabetes mellitus and tobacco use. Only 1 percent of adults age 50 to 59 have significantly narrowed carotid arteries, but 10 percent of adults age 80 to 89 have this problem.

Arteries are normally smooth and unobstructed on the inside, but as one ages, fat can accumulate in the walls of the artery causing inflammation. This combination leads to the development of a plaque. Plaque is made up of inflammatory and smooth muscle cells as well as cholesterol, calcium, and fibrous tissue. As more plaque builds up, the arteries narrow and stiffen. This process is called atherosclerosis, or hardening of the arteries.

Some plaque deposits are soft and are prone to cracking or forming roughened, irregular areas inside the artery. Cracking, or rupture, of an atherosclerotic plaque exposes material that promotes clot formation to the blood flow. Thus, a large blood clot may then form in the artery, such as in distal common or proximal internal carotid artery or one of its branches. If the clot blocks the artery enough to slow or stop blood and oxygen flow to the brain, it could cause a stroke. More commonly, a piece of the plaque itself, or a clot, breaks off from the plaque deposit and travels through the bloodstream. This particle can then lodge in a smaller artery in the brain and cause a stroke by blocking the artery.

Thus far, the only approved acute pharmacologic intervention for AIS, intravenous alteplase (recombinant tissue plasminogen activator or rtPA). The use of this compound in the emergency department is unique because of its extremely narrow temporal window and strict contraindications, and it has been estimated that just 3%-8% of eligible subjects with AIS receive rtPA.

Nucleic Acid Sequences

The nucleic acid sequences disclosed herein are shown using standard letter abbreviations for nucleotide bases. Only one strand of each nucleic acid sequence is shown, but the complementary strand is understood as included by any reference to the displayed strand. The Sequence Listing is submitted as an ASCII text file in the form of the file named 129715-214398_Sequence_Listing.txt, which was created on Feb. 23, 2016, is 2.56, kilobytes, and is incorporated by reference herein.

An exemplary nucleotide sequence for miR-145 is caccuugucc ucacggucca guuucccag gaaucccuua gaugcuaaga uggggauucc uggaaauacu guucuugagg ucauggu (SEQ ID NO: 1), as available at reference number NR_029686.1 from the NCBI Feb. 12, 2015.

An exemplary nucleotide sequence for miR-221 is NR_029635.1 ugaacaucca ggucugggc augaaccugg cauacaaugu agauuucugu guucguuagg caacagcuac auugucugcu gggguuucagg cuaccuggaa acauguucuc (SEQ ID NO: 2), as available at reference number NR_029635.1 from the NCBI Feb. 12, 2015.

An exemplary nucleotide sequence for miR-222 is gcugcuggaa gguguaggua cccucaaugg cucaguagcc aguguagauc cugucuuucg uaaucagcag cuacaucugg cuacuggguc ucugauggca ucuucuagcu (SEQ ID NO: 3), as available at reference number NR_029636.1 from the NCBI Feb. 12, 2015.

An exemplary nucleotide sequence for circR-284, also known as circR-16 is:

```
                                                     (SEQ ID NO: 4)
gguauggccucacaagucuuggucuacccaccauauguuuaucaaacuc agucaagugccuuuuguagugugaagaaacucaaaguagagccaagcag uuguguauuccaggaaagaaacuauccacggaccuaugugaaugguaga aacuuuggaaauucucauccucccacuaagggguagugcuuuucagacaa agauaccauuuaauagaccucgaggacacaacuuuucauugcagacaag ugcuguuguuuugaaaaacacugcaggugcuacaaaggucauagcagcu caggcacagcaagcucacgugcaggcaccucagauuggggcguggcgaa acagauugcauuccuagaaggccccccagcgaugugauugaagcgcaa gagugaggaguuggauaaucauagcagcgcaaugcagauugucgaugaa uuguccauacuuccugcaauguugcaaaccaacaugggaaauccaguga caguugugacagcuaccacaggaucaaaacagaauuguaccacuggaga
```

-continued aggugacuaucaguuaguacagcaugaagucuuaugcuccaugaaaaau acuuacgaaguccuugauuuucuuggucgaggcacguuuggccagguag uuaaaugcuggaaaagagggacaaaugaaauuguagcaaucaaaauuuu gaagaaucauccuucuuuaugcccgucaaggucaaauagaagugagcaua uuagcaaggcucaguacugaaaaugcugaugaauauaacuuuguacgag cuuaugaaugcuuucagcaccguaaccauacuuguuuagucuuugagau gcuggaacaaaacuuguaugacuuucugaaacaaaauaaauuuaguccc cugccacuaaaagugauucggcccauucuucaacaaguggccacugcac ugaaaaaauugaaaagucuugguuuaauucaugcugaucucaagccaga gaauauuauguugguggauccuguucggcagccuuacagggguuaaagua auagacuuugggucggccagucauguaucaaagacuguuuguucaacau aucuacaaucucgguacuacag.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

FIG. 2C is a bar graph comparing normalized ratios of serum circR-284 to serum miR-221 in asymptomatic and urgent (ischemic event occurring within last five days) carotid subjects, showing orders of magnitude higher ratios in the latter group.

DETAILED DESCRIPTION OF DISCLOSED EMBODIMENTS

Terms

Figure 1:
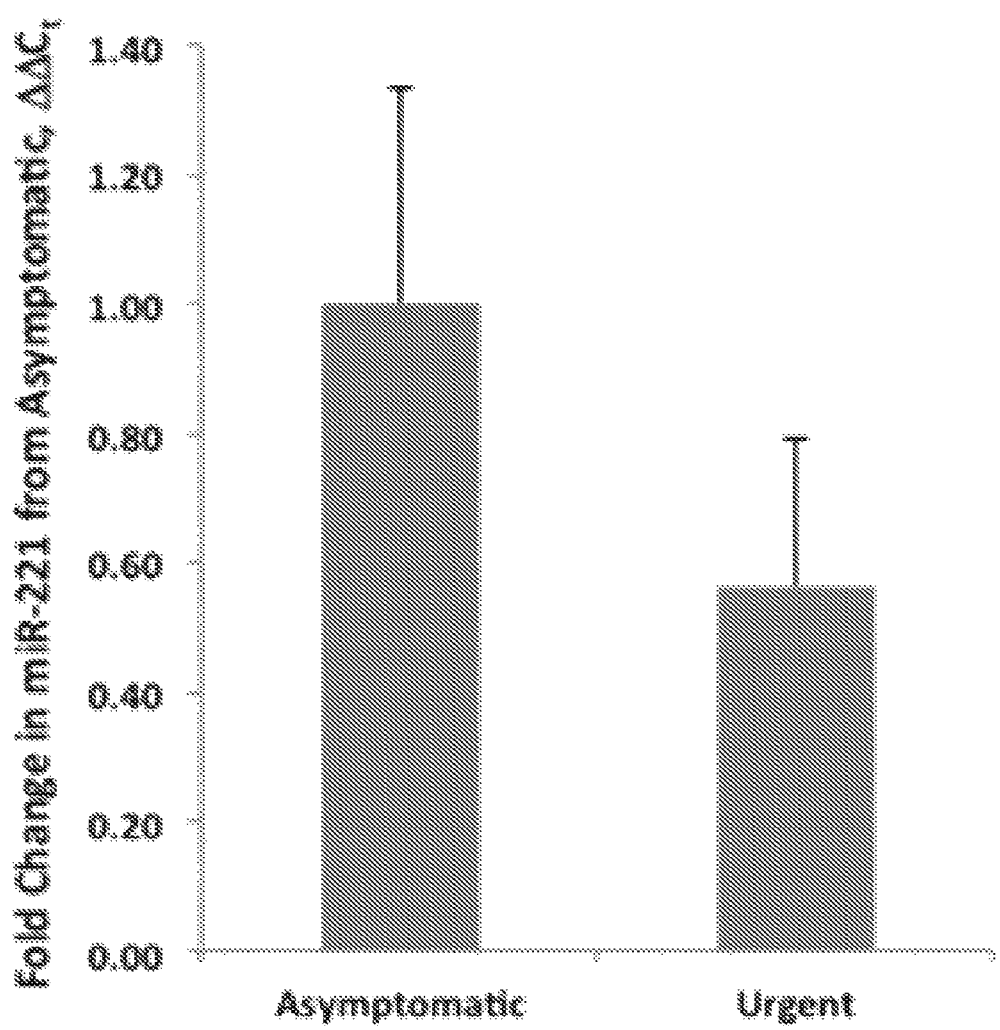
FIG. 1 is a bar graph comparing ΔΔCt serum measurements of miR-221 in asymptomatic and urgent carotid subjects, showing miR-221 levels are decreased in the latter group; patients presenting with an acute ischemic cerebral event (transient ischemic attack [TIA] or AIS) and undergoing an expedited carotid endarterectomy (CEA) surgery.

In the following detailed description, reference is made to the accompanying drawings that form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology,* Greene Publishing Associates, 1992 (and Supplements to 2000); Ausubel et al., *Short Protocols in Molecular Biology: A Compendium of Methods from Current Protocols in Molecular Biology,* 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999. In addition, the materials, methods, and examples are illustrative only and not intended to be limiting.

To facilitate review of the various embodiments of the disclosure, the following explanations of specific terms are provided:

Administration: To provide or give a subject an agent, such as a therapeutic agent, by any effective route. Exemplary routes of administration include, but are not limited to, injection (such as subcutaneous, intramuscular, intradermal, intraperitoneal, and intravenous), oral, intraductal, sublingual, rectal, transdermal, intranasal, and inhalation routes.

Agent: Any protein, nucleic acid molecule (including chemically modified nucleic acids), compound, small molecule, organic compound, inorganic compound, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject, including inhibiting or treating an ischemic event, such as stroke or myocardial infarction). In some examples, the therapeutic agent includes a tissue plasminogen activator tPA, isolated miR gene product that is down-regulated in patients with an ischemic event or an inhibitor of a circR that is up-regulated in patients with an ischemic event.

Alteration in expression: An alteration in expression of a miR gene product or circR gene product refers to a change or difference, such as an increase or decrease, in the level of the miR gene product or circR gene product, that is detectable in a biological sample (such as a sample from subject, for example a serum sample), for example relative to a control, such as a subject not suffering arterial plaque rupture. An "alteration" in expression includes an increase in expression (up-regulation) or a decrease in expression (down-regulation). In some examples, an alteration in expression includes a change or difference, such as an increase or decrease, in the conversion of the information encoded in a miR gene into miR gene product or a circR gene into circR gene product. In some examples, the difference is relative to a control or reference value, such as an amount of miR and/or circR expression in a sample from a healthy control subject.

Antisense compound: An oligomeric compound that is at least partially complementary to the region of a target nucleic acid molecule (such as a miR or circR gene product) to which it hybridizes. As used herein, an antisense compound that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulate expression. In some examples, the target nucleic acid molecule is a circR gene product (such as circR-284).

Nonlimiting examples of antisense compounds include primers, probes, antisense oligonucleotides, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self-complementarity to allow for hybridization and formation of a fully or partially double-stranded compound. In particular examples herein, the antisense compound is an antisense oligonucleotide, siRNA or ribozyme.

In some examples, an antisense compound is an "antisense oligonucleotide." An antisense oligonucleotide is a single-stranded antisense compound that is a nucleic acid-based oligomer. An antisense oligonucleotide can include one or more chemical modifications to the sugar, base, and/or internucleoside linkages. Generally, antisense oligonucleotides are "DNA-like" such that when the antisense oligonucleotide hybridizes to a target RNA molecule, the duplex is recognized by RNase H (an enzyme that recognizes DNA:RNA duplexes), resulting in cleavage of the RNA.

Array: An arrangement of molecules, such as biological macromolecules (such nucleic acid molecules, for example probes), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from at least 2, at least 5, at least 10, at least 14, at least 15, at least 20, at least 30, at least 50, at least 75, at least 100, at least 150, at least 200, at least 300, at least 500, least 550, at least 600, at least 800, at least 1000, at least 10,000, or more. In a particular example, an array includes 5-1000 addressable locations, such as 10-100 addressable locations. In particular examples, an array consists essentially of probes or primers (such as those that permit amplification) specific for the miR gene products and/or circR gene product discussed herein.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Biological sample: A biological specimen containing genomic DNA, RNA (including mRNA, microRNA and/or circRNA), protein, or combinations thereof, obtained from a subject. Examples include, but are not limited to, saliva, peripheral blood, urine, tissue biopsy, surgical specimen, and autopsy material. In embodiments, the biological sample is blood, or a component thereof, such as plasma or serum.

Circular RNA (or circRNA or circR): A type of RNA which, unlike the better known linear RNA, forms a covalently closed continuous loop, i.e., in circular RNA the 3' and 5' ends normally present in an RNA molecule have been joined together. This feature confers numerous properties to circular RNAs, many of which have only recently been identified. Many circular RNAs arise from otherwise protein-coding genes, but circular RNAs produced in the cell have not been shown to code for proteins. They have therefore been categorized as noncoding RNA. Some circular RNAs have recently shown potential as gene regulators.

Because circular RNAs do not have 5' or 3' ends, they are resistant to exonuclease-mediated degradation and are presumably more stable than most linear RNAs in cells.

Contacting: Placement in direct physical association, including both a solid and liquid form. Contacting an agent with a cell can occur in vitro by adding the agent to isolated cells or in vivo by administering the agent to a subject.

Control: A "control" refers to a sample or standard used for comparison with a test sample, such as a sample obtained from a subject or patient (or plurality of patients). In some embodiments, the control is a sample obtained from a healthy patient (or plurality of patients) (also referred to herein as a "normal" control). In some embodiments, the control is a historical control or standard value (e.g. a previously tested control sample or group of samples that represent baseline or normal values, such as baseline or normal values in a normal subject or subject in which an arterial plaque has not ruptured). In some examples the control is a standard value representing the average value (or average range of values) obtained from a plurality of patient samples (such as an average value or range of values of miR or circR expression from normal patients).

Decrease or downregulate: To reduce the quality, amount, or strength of something. In some examples, when used in reference to the expression of nucleic acid molecules (such as a miR or circR), a reduction or downregulation refers to any process which results in a decrease in production of a gene product. Gene downregulation includes any detectable decrease in the production of a gene product. In certain examples, production of a miR, such as miR-221 or mir-222 or a circR, such as circR-284 decreases by at least 2-fold, at least 3-fold, at least 4-fold, at least 5-fold, at least 6-fold, at least 8-fold, at least 10-fold, at least 15-fold, at least 20-fold, at least 30-fold or at least 40-fold, as compared to a control.

Diagnosis: The process of identifying a disease by its signs, symptoms and/or results of various tests. The conclusion reached through that process is also called "a diagnosis." Forms of testing commonly performed include blood tests, medical imaging, genetic analysis, urinalysis, biopsy and the methods disclosed herein.

Diagnostically significant amount: As used herein a "diagnostically significant amount" refers to an increase or decrease in the level of a miR gene and/or circR gene product or ratio thereof in a biological sample that is sufficient to allow one to distinguish one patient population from another (such as a subject suffering an arterial plaque rupture from one that is not). In some embodiments, the diagnostically significant increase or decrease is at least 2-fold, at least 3-fold, at least 4-fold, at least 5-fold, at least 6-fold, at least 8-fold, at least 10-fold, at least 15-fold, at least 20-fold, at least 30-fold or at least 40-fold relative to a control. In some embodiments, the diagnostically significant increase or decrease is at least 2-fold, at least 3-fold, at least 4-fold, at least 5-fold, at least 6-fold, at least 8-fold, at least 10-fold, at least 15-fold, at least 20-fold, at least 30-fold or at least 40-fold change in the ratio of two or more biomarkers relative to a control.

Effective amount: An amount of agent that is sufficient to generate a desired response, such as reducing or inhibiting one or more signs or symptoms associated with a condition or disease. When administered to a subject, a dosage will generally be used that will achieve target tissue concentrations. In some examples, an "effective amount" is one that treats one or more symptoms and/or underlying causes of any of a disorder or disease.

Measuring the level of expression: As used herein, measuring the level of expression of a particular miR or circR refers to quantifying the amount of the miR or circR present in a sample. Quantification can be either numerical or relative. Detecting expression of the miR or mRNA can be achieved using any method known in the art or described herein, such as by RT-PCR. Detecting expression of a miR or circR includes detecting expression of either a mature form of the miR, or circR or a precursor form (i.e., a pri-miR or pre-miR, or pri-circR or pre-circR) that is correlated with expression of the miR or circR. Typically, miR and circR detection methods involve sequence specific detection, such as by RT-PCR. miR-specific primers and probes can be designed using the precursor and mature miR and circR nucleic acid sequences that are known in the art (the miRBase microRNA database is available online by the University of Manchester at www.mirbase.org and the circBase circR database is available online at www.circbase.org).

In embodiments, the change detected is an increase or decrease in expression as compared to a control, such as a reference value or a healthy control subject. In some examples, the detected increase or decrease is an increase or decrease of at least two-fold compared with the control or standard. Controls or standards for comparison to a sample, for the determination of differential expression, include samples believed to be normal as well as laboratory values (e.g., range of values), even though possibly arbitrarily set, keeping in mind that such values can vary from laboratory to laboratory.

Laboratory standards and values can be set based on a known or determined population value and can be supplied in the format of a graph or table that permits comparison of measured, experimentally determined values.

MicroRNA (miRNA or miR): A single-stranded RNA molecule that regulates gene expression in plants, animals and viruses. A gene encoding a microRNA is transcribed to form a primary transcript microRNA (pri-miR), which is processed to form a short stem-loop molecule, termed a precursor microRNA (pre-miR), followed by endonucleolytic cleavage to form the mature microRNA. Mature microRNAs are approximately 21-23 nucleotides in length and are partially complementary to the 3'UTR of one or more target messenger RNAs (mRNAs). The term "microRNA gene product" includes pri-miRs, pre-miRs and mature microRNAs (including minor mature miR species referred to as miR*). MicroRNAs modulate gene expression by promoting cleavage of target mRNAs or by blocking translation of the cellular transcript.

Patient or Subject: A term that includes human and non-human animals, such as those having arterial plaques. In one example, the patient or subject is a mammal, such as a human. "Patient" and "subject" are used interchangeably herein.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 19th Edition (1995), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Small interfering RNA (siRNA): A double-stranded nucleic acid molecule that modulates gene expression through the RNAi pathway (see, for example, Bass, Nature 411:428-9, 2001; Elbashir et al., Nature 411:494-8, 2001; and PCT Publication Nos. WO 00/44895; WO 01/36646; WO 99/32619; WO 00/01846; WO 01/29058; WO 99/07409; and WO 00/44914). siRNA molecules are generally 20-25 nucleotides in length with 2-nucleotide overhangs on each 3' end. However, siRNAs can also be blunt ended. Generally, one strand of a siRNA molecule is at least partially complementary to a target nucleic acid, such as a target circRNA. siRNAs are also referred to as "small inhibitory RNAs," "small interfering RNAs" or "short inhibitory RNAs." As used herein, siRNA molecules need not be limited to those molecules containing only RNA, but further encompasses chemically modified nucleotides and non-nucleotides having RNAi capacity or activity. In an example, a siRNA molecule is one that reduces or inhibits the biological activity or expression of a circR gene product.

Treating a disease: A phrase referring to a therapeutic intervention that ameliorates a sign or symptom of a disease or pathological condition after it has begun to develop.

Upregulated or activated: When used in reference to the expression of a nucleic acid molecule (such as a miR or circR), refers to any process which results in an increase in production of a gene product. In the context of the present disclosure, a gene product can be a primary transcript ncRNA, precursor ncRNA, or a mature ncRNA, such as a miR or circR. Gene upregulation or activation includes any detectable increase in any of these molecules. In certain examples, production of a ncRNA such as a circR increases by at least 2-fold, at least 3-fold, at least 4-fold, at least 5-fold, at least 6-fold, at least 8-fold, at least 10-fold, at least 15-fold, at least 20-fold, at least 30-fold or at least 40-fold, as compared to a control.

Overview of Several Embodiments

There currently is a limited understanding of the mechanisms involved in atherosclerotic plaque rupture. This lack of knowledge is a critical barrier to developing new therapies for the prevention of complications of atherosclerosis. A strategy for developing new therapies and/or providing early intervention is biomarker measurement in subjects presenting with stroke or stroke-like symptoms. For example prior to the extensive work-up that ensues in order to determine whether a plaque rupture has occurred.

In the carotid artery, atherosclerotic plaque rupture leads to stroke, a complication of atherosclerosis. In the coronary bed, plaque rupture results in a myocardial infarction. Thus, early detection of plaque rupture through biomarker measurement may reduce the morbidity and mortality in subjects suffering from atherosclerosis. Prior to this disclosure, biomarkers and specifically serum biomarker(s) for atherosclerotic plaque rupture and acute stroke were unknown.

Fibrous cap formation and atherosclerotic plaque stability is regulated, in part, by alterations in the expression of non-coding RNAs with in the arterial wall. The inventors have discovered that certain changes in expression are mirrored in the serum of subjects during atherosclerotic carotid plaque rupture. As disclosed herein, the inventors determined that changes in the expression of non-coding RNAs within carotid plaques were reflected in the serum of subjects pre- and post-carotid-related ischemic stroke. Specifically, they have discovered that there a changes in the levels of certain RNAs in subject, such as changes in the levels of micro RNAs (miRs) and circular RNAs (circRs).

miRs regulate gene expression and protein translation and can thus provide new venues for therapeutic targets. miRs are non-coding RNAs (ncRNAs), a novel class of endogenous small RNAs that negatively regulate gene expression via degradation or translational inhibition of their target transcripts (mRNAs). circRs on the other hand, are believed to regulate miRs by acting as 'sponges' or decoys, further regulating gene expression, providing multiple levels of control.

In plaque development circRs appear to regulate miRs. As disclosed herein, the expression of at least two microRNAs, including miR-221 and miR-222, is diminished and the expression of circR-284, an inhibitor of miR-221 and miR-222, is increased in atherosclerotic plaque rupture. As shown in FIG. 1, it was found that miR-221 is decreased in the sera of subjects undergoing urgent carotid endarterectomys (CEAs), correlating with the changes present in the carotid plaque itself. Analysis of three different miRs involved in intimal thickening revealed that only miR-221 is decreased in the sera of subjects with acute neurological symptoms, compared to asymptomatic subjects with high-grade carotid stenosis.

Figure 2A:
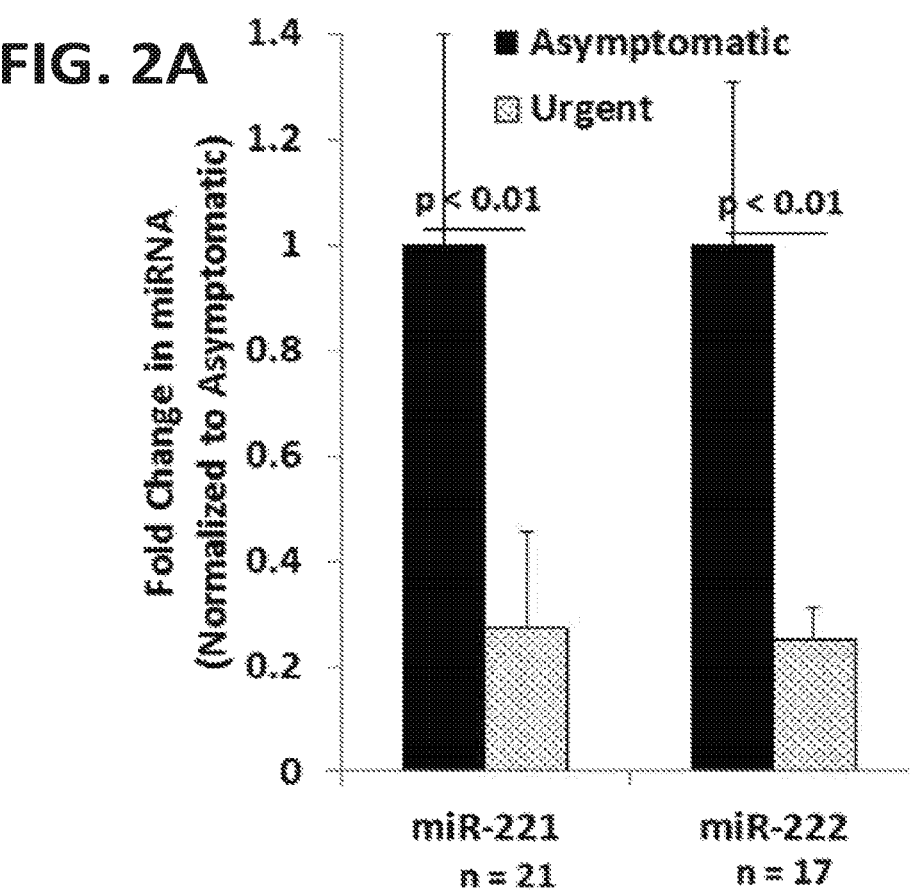
FIG. 2A is a bar graph comparing normalized serum measurements of miR-221 and miR-222 in asymptomatic and urgent (ischemic event occurring within last five days) carotid subjects, showing lower levels of both biomarkers in the latter group. The fold-change decreases in the urgent group are normalized to the asymptomatic group.
Figure 2B:
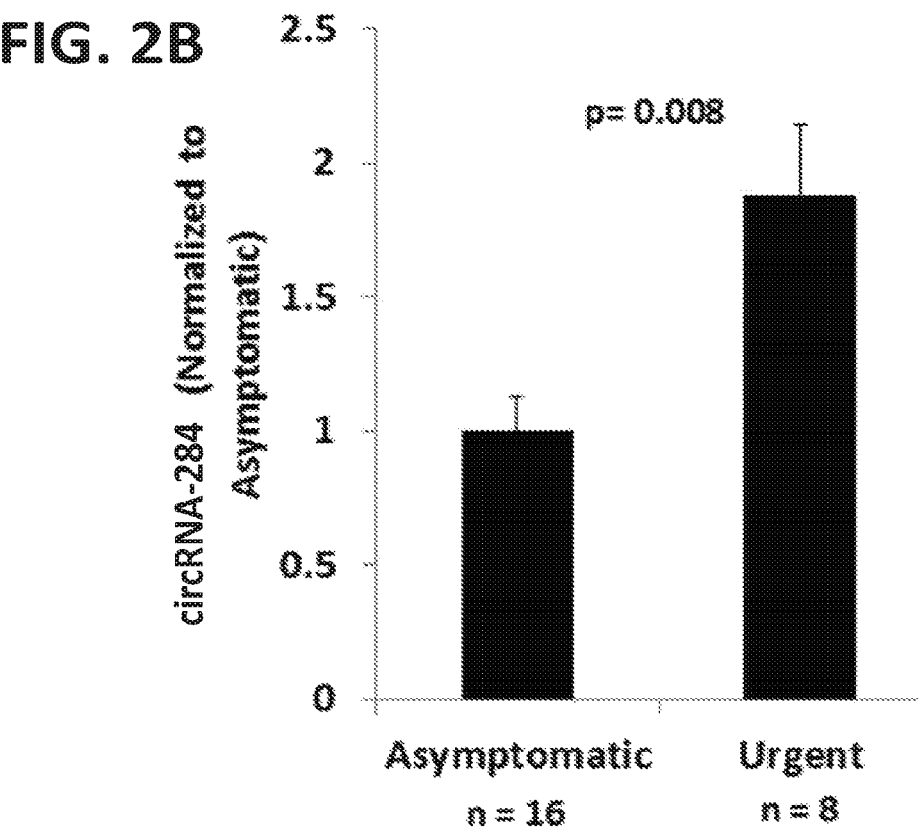
FIG. 2B is a bar graph comparing normalized serum measurements of circR-284 in asymptomatic and urgent (ischemic event occurring within last five days) carotid subjects, demonstrating higher levels of circR-284 in the latter group.
Figure 3:
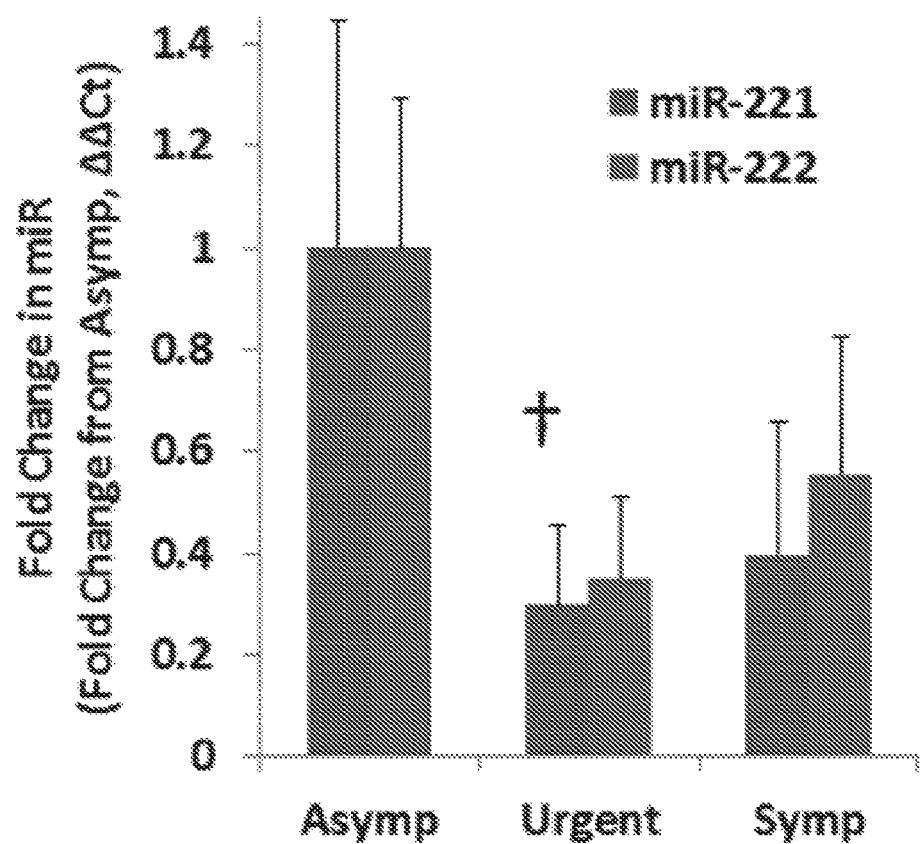
FIG. 3 is a bar graph comparing normalized serum measurements of miR-221 and miR-222 in asymptomatic, urgent (ischemic event occurring within last five days), and symptomatic (elective) carotid subjects, showing lower levels of both biomarkers in the latter groups, urgent and symptomatic. Note that the levels of miR-221 and -222 are decreased in symptomatic patients and the more profound decrease is noted in the acutely symptomatic patients.
Figure 4A:
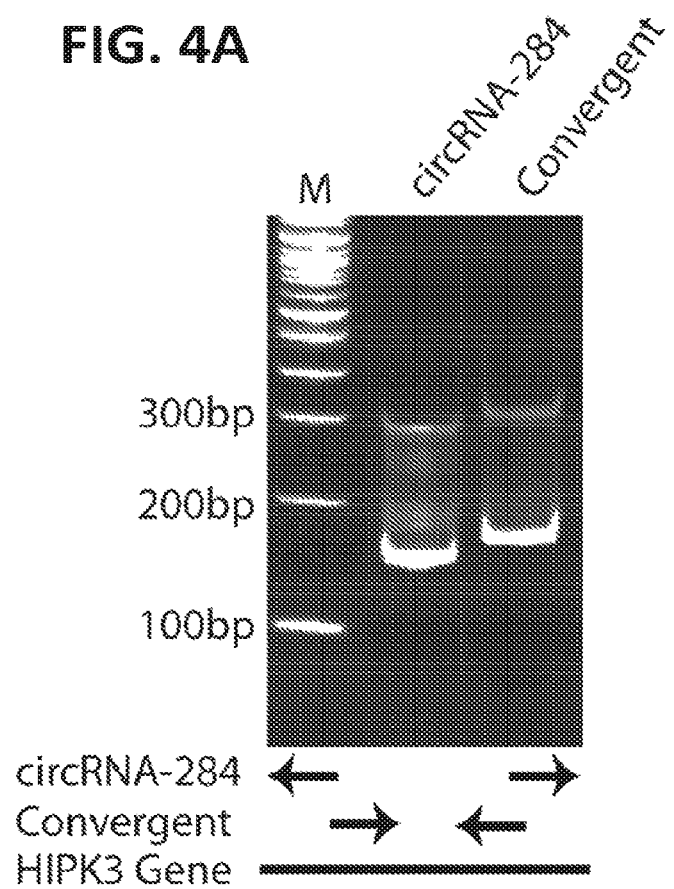
FIG. 4A is a digital image of a gel showing reverse transcriptase polymerase chain reaction (RT-PCR) results from primers for circR-284 and convergent primers that detect the linear mRNA transcript in lysates of human aortic vascular smooth muscle cells.
Figure 4B:
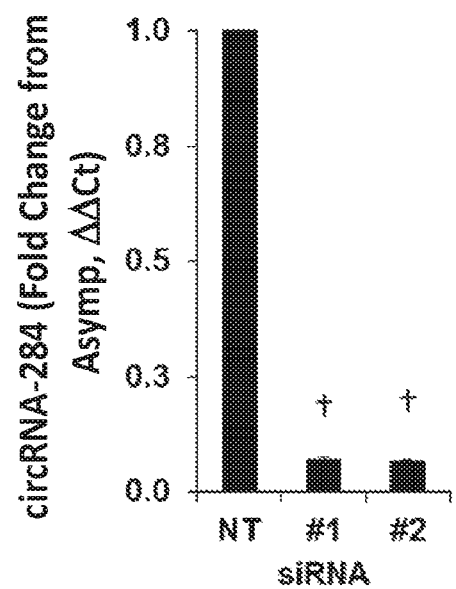
FIG. 4B is a bar graph showing that circR-284 is sensitive to knockdown by siRNA methods.
Figure 4C:
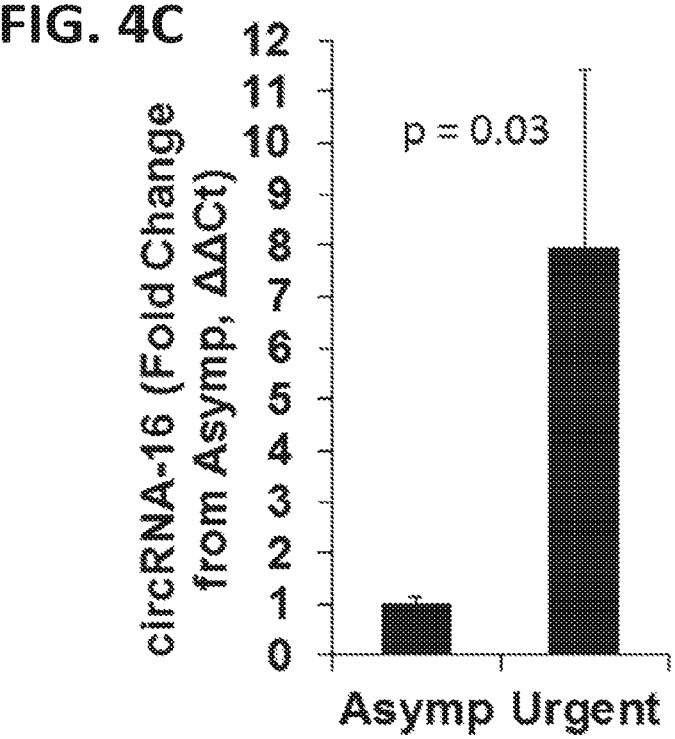
FIG. 4C is a bar graph comparing normalized serum measures of circR-284 in asymptomatic and urgent (ischemic event occurring within last five days) carotid subjects.
Figure 4D:
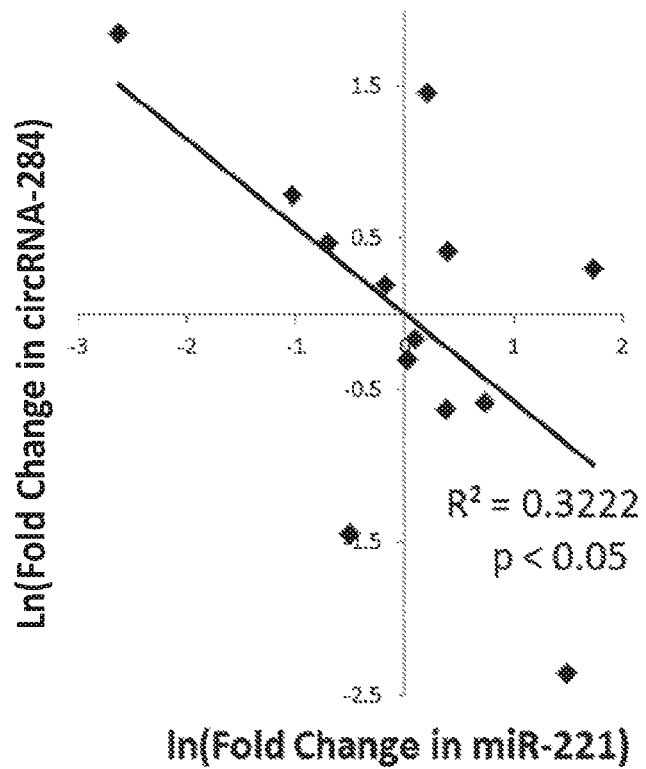
FIG. 4D is a scatter plot showing that fold changes in circR-284 and miR-221 in carotid artery plaques inversely correlate. circR-284 was measured using quantitative RT-PCR with hypoxanthine phosphoribosyltransferase 1 as loading control.

Furthermore, as shown in FIGS. 2A-2C and 3, carotid plaque rupture ('urgent' subjects, n=21) was accompanied by a 4-fold drop in miR-221 and miR-222 levels within the carotid plaque shoulder, compared to the plaques in asymptomatic subjects (n=17, FIG. 2A, P<0.05). In contrast, circR-284 was increased 1.9±0.3-fold in urgent plaque shoulders (n=8) compared to asymptomatic plaque shoulders (n=16, FIG. 2B, P=0.008). Similar changes in ncRNAs were observed in the sera of these subjects: miR-221 is increased in asymptomatic (n=19) compared to acutely symptomatic/urgent subjects (n=15); and, increased circR-284 RNA levels are present in the urgent (n=6) compared to the asymptomatic (n=6) group. Lastly, normalizing circR-284 to miR-221 levels in the serum yielded a value that was significantly increased in urgent compared to asymptomatic groups (FIG. 3C-Whisker plot, P=0.03). Finally, as is shown in FIGS. 4A-4D, certain circRs negatively regulate specific miRs. For example FIGS. 4A and 4B show that circR-284 is expressed by human vascular smooth muscle cells and that its expression may be repressed using silencing RNA. In contrast to miR-221/222, circR-284 is increased in the urgent group compared to the asymptomatic group (see FIG. 4C). In addition, it was found that miR-221 expression inversely correlates with circR-284 expression in the carotid plaques (see FIG. 4D). Taken together, these data indicate that circR-284 mediates the repression of miR-221/222 seen with plaque rupture.

Clinically, measuring these ncRNAs in subjects presenting with stroke symptoms has the advantage of determining whether an atherosclerotic plaque rupture (such as, from the carotid artery plaque) is the culprit as opposed to other etiologies (such as, cardiac emboli, dysrrhythmias, cryptogenic stroke, etc), thereby decreasing delays in time to diagnosis. For example subjects diagnosed with an ischemic stroke within 3 hours may be offered systemic thrombolysis with recombinant tissue plasminogen activator (tPA), which has improved outcomes after stroke (Saver et al., JAMA. 2013; 309:2480-2488). However, tPA utilization rates among acute ischemic stroke subjects is currently only 7% due to delay in diagnosis of greater than 3 hours (Schwamm et al., Circulation. Cardiovascular quality and outcomes. 2013). A rapid diagnostic method, such as disclosed herein, would have the potential to minimize diagnostic delays and increase the tPA utilization rate, improving outcomes. Thus, the methods disclosed herein enhance more expeditious definitive treatment (such as, thrombolysis with tissue plasminogen activator [tPA], rapid carotid revascularization, and, in some cases, urgent carotid endarterectomy). It also has tremendous cost-saving to the health system as it would identify the source of the stroke prior to an expensive clinical work-up, including computed tomography (CT) scans of the head, magnetic resonance imaging (MRI) of the neck and brain, CT angiography, etc.

The applicants have also developed novel methods for identifying and measuring biomarkers to predict and/or detect atherosclerotic plaque rupture. Carotid atherosclerotic plaque rupture is accompanied by a loss of miR-221/222 and an increase in circR-284 RNA levels and that these changes are observable in the sera. The applicants' methods, described in greater detail below, may identify other ncR-NAs (i.e. miRs, circRs) that are uniquely involved in both asymptomatic carotid disease and during carotid plaque rupture.

These methods may include identifying threshold value(s) for:

1) an equation that combines levels of a set of ncRNAs (either increases or decreases) to predict plaque rupture, 2) a ratio of two or more ncRNAs that is predictive of plaque rupture, 3) a ratio of one or more ncRNAs with a normalization factor (e.g. serum creatinine), and/or 4) a ratio of one or more ncRNA with a biomarker of inflammation (e.g. C-reactive protein). For example, using the second type of method, the ratio of miR-221 and/or miR-222 to miR-145 may be used as a biomarker of plaque rupture.

Methods of Detecting Arterial Plaque Rupture

Provided herein is a method of detecting an arterial plaque rupture in an artery of a subject by measuring the level of at least one miR gene product and one circR in a biological sample obtained from the subject. In embodiments, at least one miR gene product includes any either or both of a miR-222 or a miR-221 gene product. In embodiments, the circR gene product is circR-284. While the levels of these biomarkers present in serum were found to be altered during, or after, arterial plaque rupture, the inventors further found that the ratio of the miR and the circR was particularly predictive in detecting arterial plaque rupture. Thus, in embodiments, the ratio of the expression of level of circR-284 to the expression level of at least one of miR-221 and miR-222 is determined or calculated. A ratio of circR-284 to miR-221 or miR-222 greater than a reference value indicative of a no rupture indicates that the subject has experienced arterial plaque rupture. In some embodiments, an increase in the level of circR-284 indicates arterial plaque rupture, for example relative to a control. In embodiments, a decrease in the level of miR-221 and/or miR-222 indicates arterial plaque rupture, for example relative to a control. In some embodiments, the increase or decrease in the level of the miR or circR is of a diagnostically significant amount. In embodiments, the expression of miR-221 is detected. In embodiments, the expression of miR-221 is detected. In embodiments, the expression of miR-145 is detected.

In some embodiments of the methods, the diagnostically significant increase or decrease in expression of the circR or miR gene product is at least a 1.1-fold, 1.2-fold, 1.3-fold, 1.4-fold, 1.5-fold, 2-fold, 3-fold, 4-fold, 5-fold, 10-fold increase or decrease, for example relative to the level of a control. In some example the ratio of the circR to miR is at least 1.1, 1.2, 1.3, 1.4, 1.5, 2, 3, 4, 5, 6, 7, 8, 9, 10, 15, 20, 30, 50, 60, 70, 80, 100, or even greater. Thus in some embodiments, the ratio of the circR to miR of at least 1.1, 1.2, 1.3, 1.4, 1.5, 2, 3, 4, 5, 6, 7, 8, 9, 10, 15, 20, 30, 50, 60, 70, 80, 100, or even greater is used as a control threshold, above which a plaque rupture is diagnosed or detected.

In addition methods are disclosed herein may be used to find other biomarkers to predict and/or detect atherosclerotic plaque rupture. Comparing absolute or relative concentrations of ncRNA in the serum is complicated by differing blood volumes in subjects. To overcome this, normalization strategies may be used to determine the relative concentration (ratio) of one ncRNA of interest to another. In this method, normalized cycle threshold ($\Delta C_t$) is calculated by one of the methods below. A direct ratio of two ncRNA of interest may be determined using the equation:

$$\Delta C_t = C_{t,G1} - C_{t,G2}$$

Where:
$C_{t,G1}$=Cycle threshold for ncRNA of interest 1; and
$C_{t,G2}$=Cycle threshold for ncRNA of interest 2.
Normalized ratios may be determined using the equation:

$$\Delta C_t = (C_{t,G1} - C_{t,HK1}) - (C_{t,G2} - C_{t,HK2}).$$

Where:
$C_{t,G1}$=Cycle threshold for ncRNA of interest 1;
$C_{t,G2}$=Cycle threshold for ncRNA of interest 2;
$C_{t,HK1}$=Cycle threshold for spike-in control RNA 1; and
$C_{t,HK2}$=Cycle threshold for spike-in control RNA 2.

For example, using the foregoing normalized ratio method, subjects that had a plaque rupture within the last 5 days were found to exhibit a 77 fold higher ratio of circR-284 to miR-221. See FIG. 2C.

The fold difference between the test $\Delta C_t$ and a $\Delta C_t$ for the control sample may be determined using the equation: Fold difference=$2^{-(\Delta C_{t test} \Delta C_{t control})}$. For example, see FIGS. 1, 2A, and 3.

Methods of detecting and measuring miR and circR expression are known in the art and are described in detail below. In some examples, RT-PCR is used to measure the level of a miR and/or circR, such as when a single miR or circR is analyzed. In other cases, when multiple miR gene products and/or circR are to be measured, it may be desirable to use microarray analysis.

The miR gene product measured can be a primary miR (pri-miR) precursor miR (pre-miR), or a mature miR (including minor mature miR products denoted miR*). The circR gene product measured can be a primary circR (pri-circR) precursor miR (pre-circR), or a mature circR (including minor mature circR products denoted circR*). In some examples, the nucleic acid sequences set forth as SEQ ID NOS; 1-4 above, or subsequences thereof or measured or determined.

In some embodiments of the methods, the biological sample is blood, or a component thereof, such as plasma or serum. Thus, the method in some examples includes obtaining an appropriate sample from the patient to be diagnosed or treated with the methods provided herein.

In some embodiments, the method further includes providing an appropriate therapy for the subject diagnosed with an arterial plaque rupture. In some examples, the therapy includes administering an isolated miR gene product, such a miR gene product that has been identified as down-regulated in arterial plaque rupture relative to a control. In some examples, the therapy includes administering an agent that inhibits expression of a circR gene product, such as an agent that inhibits a circR gene product identified as up-regulated in arterial plaque rupture relative to a control. In other examples, the therapy includes administering an agent that includes administering tissue plasminogen activator (tPA) to the subject. In some embodiments, the therapy includes surgical intervention or a recommendation of such intervention, such as rapid carotid revascularization, carotid endarterectomy, bypass surgery or other surgical interventions known in the art.

In some embodiments, the method includes selecting a subject with, or believed to have, suffered a stroke. In some embodiments, the method includes selecting a subject with, or believed to have, suffered a myocardial infarction. In some embodiments, the method is used for diagnosing or prognosing a subject with stroke and/or myocardial infarction. In some embodiments, the method includes selecting a subject with, or believed to have, suffered an arterial plaque rupture, or at risk for such a rupture.

In some embodiments, once a patient's diagnosis is determined, an indication of that diagnosis can be displayed and/or conveyed to a clinician or other caregiver. For example, the results of the test are provided to a user (such as a clinician or other health care worker, laboratory personnel, or patient) in a perceivable output that provides information about the results of the test. In some examples, the output is a paper output (for example, a written or printed output), a display on a screen, a graphical output (for example, a graph, chart, voltammetric trace, or other diagram), or an audible output. In other examples, the output is a numerical value, such as an amount of miR and/or circR expression in the sample or a relative amount of miR and/or circR in the sample as compared to a control. In some examples the numerical value is the ratio of expression of miR to circR. In additional examples, the output is a graphical representation, for example, a graph of the expression and/or ratio of expression on a standard curve or ROC. In a particular example, the output (such as a graphical output) shows or provides a cut-off value or level that indicates the presence of arterial plaque rupture. In some examples, the output is communicated to the user, for example by providing an output via physical, audible, or electronic means (for example by mail, telephone, facsimile transmission, email, or communication to an electronic medical record). The output can provide quantitative information. In some examples, the output is accompanied by guidelines for interpreting the data, for example, numerical or other limits that indicate the presence or absence of arterial plaque rupture. The guidelines need not specify whether arterial plaque rupture is present or absent, although it may include such a diagnosis. The output can, for example, include normal or abnormal ranges or a cutoff, which the recipient of the output may then use to interpret the results, for example, to arrive at a diagnosis, prognosis, or treatment plan. In other examples, the output can provide a recommended therapeutic regimen. In some examples, the test may include determination of other clinical information.

In some embodiments, the disclosed methods of diagnosis include one or more of the following depending on the patient's diagnosis: a) prescribing a treatment regimen for the patient if the patient's determined diagnosis is considered to be positive for arterial plaque rupture; b) not prescribing a treatment regimen for the patient if the patient's determined diagnosis is considered to be negative for arterial plaque rupture; c) administering a treatment to the patient if the patient's determined diagnosis is considered to be positive for arterial plaque rupture; and d) not administering a treatment regimen to the patient if the patient's determined diagnosis is considered to be negative for arterial plaque rupture. In an alternative embodiment, the method can include recommending one or more of a)-d). Thus, disclosed is a method of treating a stroke, transient ischemic attack (TIA), or myocardial infarction in a subject.

Kits and Assays

Also provided are kits and assays including at least two oligonucleotide probes and/or primers specific for a miR gene product and a circR gene product, such as those described below. In some embodiments, the probes and/or primers are labeled, with a detectable label. In some embodiments, the kits and assays include at least two oligonucleotide probes specific for miR-221 and/or miR-222, circR-284 and/or miR-145. In some examples, the kits and assays include controls (such as positive and negative controls). In some examples the probes and/or primers are present in an array. In some embodiments, the kits and assays include instructions for the use thereof.

Detecting miR and circR Expression

As described below, expression of one or more miRs or circRs associated with arterial plaque rupture can be detected using any one of a number of methods well known in the art. In some embodiments of the methods provided herein, miRs or circRs expression profiles are used to diagnose arterial plaque rupture and to predict the prognosis and develop potential therapies for patients with arterial plaque rupture. Thus, the disclosed methods can include evaluating miRs and circRs, such as miR-221, miR-222, miR-145 and circR-284.

The sequences of precursor miRs and circRs are publicly available, such as through the miRBase database, available online by the University of Manchester, and formerly maintained by the Sanger Institute (see Griffiths-Jones et al., *Nucleic Acids Res.* 36:D154-D158, 2008; Griffiths-Jones et al., *Nucleic Acids Res.* 34:D140-D144, 2006; and Griffiths-Jones, *Nucleic Acids Res.* 32:D109-D111, 2004) and GEN-BANK® and the database of circular RNA available at www.circbase.org. Exemplary, but not limiting, sequences are provided as SEQ ID NOS: 1-4 above.

Any one of a number of methods for detecting expression of a gene of interest (including miR and circR) known in the art can be used to detect expression of a miR and circR. A number of these methods, including qRT-PCR, array, microarray, SAGE are described in further detail below. Detection and quantification of miR and circR expression can be achieved by any one of a number of methods known in the art including those described herein (such as Example 1). U.S. Patent Application Publication Nos. 2006/0211000 and 2007/0299030 describe methods of miR detection and quantification. Further, general methods for RNA extraction are well known in the art and are disclosed in standard textbooks of molecular biology, including Ausubel et al., Current Protocols of Molecular Biology, John Wiley and Sons (1997). Using the known sequences for a miR and circR of interest, specific probes and primers can be designed for use in the detection methods described herein as appropriate.

In some cases, the miR and circR detection method requires isolation of nucleic acid from a sample, such as a blood sample, for example a serum sample. Nucleic acids, including RNA and specifically miR and circR, can be isolated using any suitable technique known in the art.

Microarray analysis of miR and circR can be accomplished according to any method known in the art (see, for example, PCT Publication No. WO 2008/054828; Ye et al., Nat. Med. 9(4):416-423, 2003; Calin et al., N. Engl. J. Med. 353(17):1793-1801, 2005). In one example, RNA is extracted from a sample, the small RNAs (18-26-nucleotide RNAs) are size-selected from total RNA using denaturing polyacrylamide gel electrophoresis. Oligonucleotide linkers are attached to the 5' and 3' ends of the small RNAs and the resulting ligation products are used as templates for an RT-PCR reaction with 10 cycles of amplification. The sense strand PCR primer has a fluorophore attached to its 5' end, thereby fluorescently labeling the sense strand of the PCR product. The PCR product is denatured and then hybridized to the microarray. A PCR product, referred to as the target nucleic acid that is complementary to the corresponding miR and circR capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miR and circR, using a number of positive and negative controls and array data normalization methods, which will result in assessment of the level of expression of a particular miR and circR.

In an alternative method, total RNA containing miR extracted from a cell, biological fluid or tissue sample is used directly without size-selection of small RNAs, and 3' end labeled using T4 RNA ligase and either a fluorescently-labeled short RNA linker. The RNA samples are labeled by incubation at 30° C. for 2 hours followed by heat inactivation of the T4 RNA ligase at 80° C. for 5 minutes. The fluorophore-labeled miRs complementary to the corresponding miR capture probe sequences on the array will hybridize, via base pairing, to the spot at which the capture probes are affixed. The microarray scanning and data processing is carried out as described herein.

Methods for quantitating RNA, including miR and circR, are well known in the art. In some embodiments, the method utilizes RT-PCR. Generally, the first step in gene expression profiling by RT-PCR is the reverse transcription of the RNA template into cDNA, followed by its exponential amplification in a PCR reaction. Two commonly used reverse transcriptases are avian myeloblastosis virus reverse transcriptase (AMV-RT) and Moloney murine leukemia virus reverse transcriptase (MMLV-RT). However, any suitable reverse transcriptase known in the art can be used for RT-PCR. The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, CA), following the manufacturer's instructions. The derived cDNA can then be used as a template in the subsequent PCR reaction.

Although the PCR step can use a variety of thermostable DNA-dependent DNA polymerases, it often employs the Taq DNA polymerase, which has a 5'-3' nuclease activity but lacks a 3'-5' proofreading endonuclease activity. Taq Man® PCR typically utilizes the 5'-nuclease activity of Taq or Tth DNA polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

To minimize errors and the effect of sample-to-sample variation, RT-PCR can be performed using an internal standard. The ideal internal standard is expressed at a constant level among different tissues, and is unaffected by the experimental treatment. RNAs commonly used to normalize patterns of gene expression are mRNAs for the housekeeping genes glyceraldehyde-3-phosphate-dehydrogenase (GAPDH), beta-actin, and 18S ribosomal RNA.

Primers that can be used to amplify a particular miR and circR are commercially available (in some instance) or can be designed and synthesized according to well-known methods using publically available sequences of the miR and circR as well as those provided herein.

SAGE is another method that allows the simultaneous and quantitative analysis of a large number of gene transcripts, without the need of providing an individual hybridization probe for each transcript. First, a short sequence tag (about 10-14 base pairs) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag (see, for example, Velculescu et al., Science 270:484-7, 1995; and Velculescu et al., Cell 88:243-51, 1997).

In particular embodiments provided herein, arrays can be used to evaluate miR and circR expression, for example to an arterial plaque rupture. When describing an array that comprises probes or primers specific for a particular set of miR and circR, such an array includes probes or primers specific for the recited microRNAs (such as miR-221, miR-222, miR-145 and circR-284), and can further include control probes (for example to confirm the incubation conditions are sufficient). In one example, an array is a multi-well plate (e.g., 98 or 364 well plate). In some embodiments, the probe and/or primers are labeled with a detectable label, for example a fluorophore, isotope, enzyme, or any other moiety that is detectable.

Modulating ncRNA Expression for Treatment or Prevention of Plaque Rupture and/or Ischemia It is disclosed herein that many ncRNAs are differentially expressed in patients with arterial plaque rupture or subject to such rupture, including patients with stroke or myocardial infarction. As such, an increase in the level of one or more miRs down-regulated in patients with arterial plaque rupture or subject to such rupture, or a decrease in the level of one or more circRs up-regulated in patients with arterial plaque rupture or subject to such rupture may be beneficial for inhibiting the development or progression of arterial plaque rupture and/or for alleviating one or more signs or symptoms associated with arterial plaque rupture (for example, stroke or myocardial infarction).

Without wishing to be bound by theory, it is believed that alterations in the level of one or more miR gene products and/or circR gene products can result in the deregulation of one or more intended targets for these miRs and circR, which can lead to undesirable effects, such as inflammation response. Therefore, altering the level of the miR gene product and/or circR (e.g., by increasing the level of a miR that is up-regulated or by decreasing the level of a circR that is down-regulated) may successfully treat or ameliorate one or more signs or symptoms of arterial plaque rupture, such as treat or ameliorate one or more signs or symptoms associated with stroke or myocardial infarction.

Provided herein is a method of treating a patient with arterial plaque rupture or subject to such rupture by administering to the patient a therapeutically effective amount of an agent that inhibits expression of a circR gene product that is up-regulated in patients with arterial plaque rupture or subject to such rupture compared with a control (such as a healthy control subject). Disclosed is a method of treating and/or preventing arterial plaque rupture or an associated inflammation response in a subject, including administering to the subject an effective amount of an agent that alters the expression of circR-284, thereby treating arterial plaque rupture and/or administering an agent that increases the expression of at least one of miR-221 and miR-222. In some examples the agent that inhibits expression of a circR gene product is an antisense compound specific for circR-284, such as an antisense oligonucleotide, siRNA or ribozyme.

As used herein, "inhibiting expression of circR gene product" means that the production of the precursor and/or active, mature form of the circR gene product after treatment is less than the amount produced prior to treatment. Expression can be altered by decreasing the levels made or degrading the amount present to reduce the level. One skilled in the art can readily determine whether circR expression has been inhibited in a subject, using the techniques known in the art and described herein. Inhibition can occur at the level of gene expression (i.e., by inhibiting transcription of a circR gene encoding the circR gene product) or at the level of processing (e.g., by inhibiting processing of a circR precursor into a mature circR).

As used herein, a therapeutically effective amount of a compound that inhibits circR expression is an amount sufficient to result in a biological effect (such as alleviating one or more signs or symptoms of arterial plaque rupture. For example, an agent can decrease or increase the expression level of a target circR by a desired amount, for example by at least 2-fold, at least 3-fold, at least 4-fold, at least 5-fold, at least 6-fold, at least 8-fold, at least 10-fold, at least 15-fold, at least 20-fold, at least 30-fold or at least 40-fold relative to a control or reference value.

One skilled in the art can readily determine a therapeutically effective amount of an agent to be administered to a given subject by taking into account several factors, such as the size and weight of the subject; the extent of disease progression; the age, health and sex of the subject; the route of administration; and whether the administration is regional or systemic. One skilled in the art can also readily determine an appropriate dosage regimen for administering to a subject an agent that inhibits expression of circR gene product.

In some embodiments, a single agent that inhibits expression of a circR gene product is administered to the subject in need of treatment. In other embodiments, two or more agents (such as 2, 3, 4, 5, 6, 7, 8, 9 or 10 or more) that inhibit expression of a circR gene product are administered to the subject. When two or more agents are administered to the subject, the agents can be administered simultaneously (or within quick succession, such as within minutes of each other), or they can be administered at different times. For example, two or more agents can be administered one hour, twelve hours, one day, two days, five days, one week, two weeks or one month apart.

An agent that inhibits expression of a circR gene product can be any type of compound, such as, but not limited to, a nucleic acid molecule, polypeptide, antibody or small molecule, that is capable of inhibiting expression of one or more circR gene products. In some embodiments, the agent is an antisense compound.

Any type of antisense compound that specifically targets a circR gene product is contemplated for use to inhibit expression of the target circR gene product. In some examples, the agent is an antisense compound selected from an antisense oligonucleotide, a siRNA, or a ribozyme. Methods of designing, preparing and using antisense compounds are within the abilities of one of skill in the art. Furthermore, sequences for the disclosed circR gene products are publicly available. Antisense compounds specifically targeting a circR that is differentially expressed, (or other target nucleic acid) can be prepared by designing compounds that are complementary to the target nucleotide sequence, such as a pri-circR, pre-circR or mature circR sequence. Antisense compounds need not be 100% complementary to the target nucleic acid molecule to specifically hybridize with the target nucleic acid molecule. For example, the antisense compound, or antisense strand of the compound if a double-stranded compound, can be at least 75%, at least 80%, at least 85%, at least 90%, at least 95%, at least 99% or 100% complementary to the selected target nucleic acid sequence. Methods of screening antisense compounds for specificity are well known in the art (see, for example, U.S. Patent Application Publication No. 2003-0228689).

Generally, the principle behind antisense technology is that an antisense compound hybridizes to a target nucleic acid and effects the modulation of gene expression activity or function. The modulation of gene expression can be achieved by, for example, target RNA degradation or occupancy-based inhibition. An example of modulation of target RNA function by degradation is RNase H-based degradation of the target RNA upon hybridization with a DNA-like antisense compound, such as an antisense oligonucleotide.

Another example of modulation of gene expression by target RNA degradation is RNA interference (RNAi) using small interfering RNAs (siRNAs). RNAi is a form of antisense-mediated gene silencing involving the introduction of double stranded (ds)RNA-like oligonucleotides leading to the sequence-specific reduction of targeted endogenous mRNA levels. Other compounds that are often classified as antisense compounds are ribozymes. Ribozymes are catalytic RNA molecules that can bind to specific sites on other RNA molecules and catalyze the hydrolysis of phosphodiester bonds in the RNA molecules. Ribozymes modulate gene expression by direct cleavage of a target nucleic acid, such as a circR gene product.

Each of the above-described antisense compounds provides sequence-specific target gene regulation. This sequence-specificity makes antisense compounds effective tools for the selective modulation of a target nucleic acid of interest, such as a circR gene product.

In some embodiments, the antisense compounds are antisense oligonucleotides. The circR gene product-specific antisense oligonucleotides can be any suitable length to allow for hybridization and modulation of gene expression. The length of an antisense oligonucleotide can vary, but is typically about 15 to about 40 nucleotides, including 15, 16, 17, 18, 19, 20, 21, 22, 23, 24, 25, 26, 27, 28, 29, 30, 31, 32, 33, 34, 35, 36, 37, 38, 39 or 40 nucleotides. In some embodiments, the antisense oligonucleotides are about 20 to about 35 nucleotides in length. The antisense oligonucleotides can be DNA, RNA or analogs thereof. Furthermore, the oligonucleotides provided herein can be unmodified or can comprise one or more modifications, such as modified internucleoside linkages, modified sugar moieties, modified bases, or a combination thereof. Oligonucleotide modifications are described in detail below.

In other embodiments, the antisense compounds are siRNA molecules. siRNAs useful for the disclosed methods include short double-stranded RNA from about 17 nucleotides to about 29 nucleotides in length, preferably from about 19 to about 25 nucleotides in length, such as about 21 to about 23 nucleotides in length. The siRNAs are made up of a sense RNA strand and a complementary antisense RNA strand annealed together by standard Watson-Crick base-pairing interactions. The sense strand includes a nucleic acid sequence that is substantially identical to a nucleic acid sequence contained within the target circR gene product. As used herein, an siRNA nucleic acid sequence that is "substantially identical" to a target sequence is a nucleic acid sequence that is identical to the target sequence, or that differs from the target sequence by one, two or three nucleotides. The sense and antisense strands of the siRNA can either include two complementary, single-stranded RNA molecules, or can be a single molecule having two complementary portions (which are base-paired) separated a single-stranded "hairpin" region.

The siRNA can also be altered RNA that differs from naturally occurring RNA by the addition, deletion, substitution and/or alteration of one or more nucleotides. Such alterations can include addition of non-nucleotide material, such as to one or both of the ends of the siRNA or to one or more internal nucleotides of the siRNA; modifications that make the siRNA resistant to nuclease digestion; or the substitution of one or more nucleotides in the siRNA with deoxyribonucleotides. One or both strands of the siRNA can also include a 3' overhang. As used herein, a "3' overhang" refers to at least one unpaired nucleotide extending from the 3'-end of a duplexed RNA strand. Thus, in certain embodiments, the siRNA includes at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA and is 2 nucleotides in length. For example, each strand of the siRNA can comprise 3' overhangs of dithymidylic acid ("TT") or diuridylic acid ("uu").

In other embodiments, the antisense compound is a ribozyme. Ribozymes are nucleic acid molecules having a substrate binding region that is complementary to a contiguous nucleic acid sequence of a circR gene product, and which is able to specifically cleave the circR gene product. The substrate-binding region need not be 100% complementary to the target circR gene product. For example, the substrate-binding region can be, for example, at least about 50%, at least about 75%, at least about 85%, or at least about 95% complementary to a contiguous nucleic acid sequence in a circR gene product. The enzymatic nucleic acids can also include modifications at the base, sugar, and/or phosphate groups.

Antisense compounds, such as antisense oligonucleotides, siRNAs and ribozymes, can be produced chemically or biologically, or can be expressed from a recombinant plasmid or viral vector, as described in further detail below in regard to expression of isolated circR gene products. Exemplary methods for producing and testing antisense compounds are well known in the art (see, for example, U.S. Pat. Nos. 5,849,902 and 4,987,071; U.S. Patent Application Publication Nos. 2002/0173478 and 2004/0018176; Stein and Cheng, Science 261:1004, 1993; Werner and Uhlenbeck, Nucl. Acids Res. 23:2092-2096, 1995; Hammann et al., Antisense and Nucleic Acid Drug Dev. 9:25-31).

In some examples, the antisense compounds specific for a circR gene product contain one or more modifications to enhance nuclease resistance and/or increase activity of the compound. Modified antisense compounds include those comprising modified backbones or non-natural internucleoside linkages. As defined herein, oligonucleotides having modified backbones include those that retain a phosphorus atom in the backbone and those that do not have a phosphorus atom in the backbone.

Examples of modified oligonucleotide backbones include, but are not limited to, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, and boranophosphates having normal 3'-5' linkages, 2'-5' linked analogs of these, and those having inverted polarity wherein the adjacent pairs of the nucleoside units are linked 3'-5' to 5'-3' or 2'-5' to 5'-2'. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Examples of modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In some embodiments, both the sugar and the internucleoside linkage of the nucleotide units of the oligonucleotide or antisense compound are replaced with novel groups. One such modified compound is an oligonucleotide mimetic referred to as a peptide nucleic acid (PNA). In PNA compounds, the sugar-backbone of an oligonucleotide is replaced with an amide containing backbone, in particular an aminoethylglycine backbone. The bases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262. Further teaching of PNA compounds can be found in Nielsen et al. (Science 254, 1497-1500, 1991).

Modified oligonucleotides can also contain one or more substituted sugar moieties. In some examples, the oligonucleotides can comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to 010 alkyl or C2 to C10 alkenyl and alkynyl. In other embodiments, the antisense compounds comprise one of the following at the 2' position: 01 to 010 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one example, the modification includes 2'-methoxyethoxy (also known as 2'-O-(2-methoxyethyl) or 2'-MOE) (Martin et al., Helv. Chim. Acta., 78, 486-504, 1995). In other examples, the modification includes 2'-dimethylaminooxyethoxy (also known as 2'-DMAOE) or 2'-dimethylaminoethoxyethoxy (also known in the art as 2'-O-dimethylaminoethoxyethyl or 2'-DMAEOE).

Similar modifications can also be made at other positions of the compound. Antisense compounds can also have sugar mimetics such as cyclobutyl moieties in place of the pentofuranosyl sugar. Representative United States patents that teach the preparation of modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920.

Oligonucleotides can also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further modified bases have been described (see, for example, U.S. Pat. No. 3,687,808; and Sanghvi, Y. S., Chapter 15, Antisense Research and Applications, pages 289-302, Crooke, S. T. and Lebleu, B., ed., CRC Press, 1993).

Certain of these modified bases are useful for increasing the binding affinity of antisense compounds. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. Representative U.S. patents that teach the preparation of modified bases include, but are not limited to, U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,750,692.

Also provided is a method of treating a patient with arterial plaque rupture or subject to such rupture by administering to the patient a therapeutically effective amount of an isolated microRNA gene product that is down-regulated in a patient with arterial plaque rupture or subject to such rupture, relative to a control (such as a healthy subject). For example, a subject with arterial plaque rupture or prone to such rupture, is treated by administering a therapeutically effective amount of an isolated miR-221 or miR-222 gene product. As described herein, the miR gene product can be a pri-miRNA, a pre-miRNA or a mature miRNA.

The disclosed methods comprise administering an effective amount of at least one isolated miR gene product, or an isolated variant or biologically-active fragment thereof. The isolated miR gene product that is administered to the subject can be identical to an endogenous wild-type miR gene product (such as a pri-miRNA, pre-miRNA or mature miRNA) that is down-regulated, or it can be a variant or biologically-active fragment thereof. As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of expression of a target RNA molecule (e.g., inhibiting translation of a target RNA molecule, modulating the stability of a target RNA molecule, or inhibiting processing of a target RNA molecule) and inhibition of a cellular process associated with arterial plaque rupture or subject to such rupture. These variants include species variants and variants that are the consequence of one or more mutations (e.g., a substitution, a deletion, an insertion) in a miR gene. In certain embodiments, the variant is at least about 70%, at least about 75%, at least about 80%, at least about 85%, at least about 90%, at least about 95%, at least about 98%, or at about 99% identical to a corresponding wild-type miR gene product.

As used herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of expression of a target RNA molecule and inhibition of a cellular process associated with arterial plaque rupture or subject to such rupture. In certain embodiments, the biologically-active fragment is at least about 9, at least about 11, at least about 13, at least about 15, at least about 17 or at least about 19 nucleotides in length.

A therapeutically effective amount of an isolated gene product can be, for example, the amount necessary to alleviate one or more signs or symptoms of a with arterial plaque rupture or subject to such rupture and/or the amount required to delay progression. One of skill in the art can determine the amount of an isolated miR gene product required for therapeutic efficacy.

In some embodiments, a single isolated miR gene product is administered to the subject in need of treatment. In other embodiments, two or more miR gene products (such as 2, 3, 4, 5, 6, 7, 8, 9 or 10 or more) are administered to the subject. When two or more miR gene products are administered to the subject, the miR gene products can be administered simultaneously (or within quick succession, such as within minutes of each other), or they can be administered at different times. For example, two or more miR gene products can be administered one hour, twelve hours, one day, two days, five days, one week, two weeks or one month apart.

In some embodiments, an isolated miR gene product can be administered to a subject in combination with one or more additional treatments for with arterial plaque rupture.

As used herein, an "isolated" miR gene product is one that is synthesized, or is purified away from other biological components of the cell or tissue in which the miR naturally occurs. For example, a synthetic miR gene product, or a miR gene product partially or completely separated from the other biological components of its natural state is considered to be "isolated." Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, for example, Proligo (Hamburg, Germany), Dharmacon Research (Lafayette, Colo.), Pierce Chemical (Rockford, Ill.), Glen Research (Sterling, VS), ChemGenes (Ashland, Mass.) and Cruachem (Glasgow, United Kingdom).

In some embodiments, the method includes administering a vector encoding a miR gene product. Vectors can be of non-viral (for example, plasmids) or viral (for example, adenovirus, adeno-associated virus, retrovirus, herpes virus, vaccinia virus) origin. Suitable vectors, such as gene therapy vectors, are well known in the art.

In some examples, the miR gene products are expressed from recombinant circular or linear DNA plasmids using any suitable promoter. Suitable promoters for expressing RNA from a plasmid include, for example, the U6 or H1 RNA pol III promoter sequences, or a cytomegalovirus promoter. Selection of other suitable promoters is within the skill in the art. The recombinant plasmids of the invention can also comprise inducible or regulatable promoters for expression of the miR gene products.

When two or more miR gene products are to be expressed, the miR gene products can each be expressed from separate recombinant plasmids, or they can be expressed from the same recombinant plasmid. In one embodiment, the miR gene products are expressed as RNA precursor molecules from a single plasmid, and the precursor molecules are processed into the functional miR gene product within the target cell. Selection of plasmids suitable for expressing the miR gene products, methods for inserting nucleic acid sequences into the plasmid to express the gene products, and methods of delivering the recombinant plasmid to the cells of interest are within the skill in the art (see, for example, Zeng et al., Mol. Cell 9:1327-1333, 2002; Tuschl, Nat. Biotechnol., 20:446-448, 2002; Brummelkarnp et al., Science 296:550-553, 2002; Miyagishi et al., Nat. Biotechnol. 20:497-500, 2002; Paddison et al., Genes Dev. 16:948-958, 2002; Lee et al., Nat. Biotechnol. 20:500-505, 2002; and Paul et al., Nat. Biotechnol. 20:505-508, 2002). In one embodiment, a plasmid expressing the miR gene product comprises a sequence encoding a miR precursor RNA operably linked to the CMV intermediate-early promoter.

The miR gene products can also be expressed from recombinant viral vectors. When administering two or more miR gene products, it is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in target cells or tissues.

The recombinant viral vectors of use with the disclosed methods include sequences encoding the miR gene products and any suitable promoter for expressing the RNA sequences. Suitable promoters include, but are not limited to, the U6 or H1 RNA pol III promoter sequences, or a cytomegalovirus promoter. Selection of other suitable promoters is within the skill in the art. The recombinant viral vectors of the invention can also comprise inducible or regulatable promoters for expression of the miR gene products.

Suitable viral vectors include, but are not limited to, adenovirus vectors, adeno-associated virus vectors, retroviral vectors, lentiviral vectors, herpesviral vectors, and the like. For example, adenovirus vectors can be first, second, third and/or fourth generation adenoviral vectors or gutless adenoviral vectors. Adenovirus vectors can be generated to very high titers of infectious particles; infect a great variety of cells; efficiently transfer genes to cells that are not dividing; and are seldom integrated in the host genome, which avoids the risk of cellular transformation by insertional mutagenesis (Zern and Kresinam, Hepatology 25(2), 484-491, 1997). Representative adenoviral vectors which can be used for the methods provided herein are described by Stratford-Perricaudet et al. (J. Clin. Invest. 90: 626-630, 1992); Graham and Prevec (In Methods in Molecular Biology: Gene Transfer and Expression Protocols 7: 109-128, 1991); and Barr et al. (Gene Therapy, 2:151-155, 1995).

Adeno-associated virus (AAV) vectors also are suitable for administration of HCC-associated genes. Methods of generating AAV vectors, administration of AAV vectors and their use are well known in the art (see, for example, U.S. Pat. No. 6,951,753; U.S. Pre-Grant Publication Nos. 2007-036757, 2006-205079, 2005-163756, 2005-002908; and PCT Publication Nos. WO 2005/116224 and WO 2006/119458).

Retrovirus, including lentivirus, vectors can also be used with the methods described herein. Lentiviruses include, but are not limited to, human immunodeficiency virus (such as HIV-1 and HIV-2), feline immunodeficiency virus, equine infectious anemia virus and simian immunodeficiency virus. Other retroviruses include, but are not limited to, human T-lymphotropic virus, simian T-lymphotropic virus, murine leukemia virus, bovine leukemia virus and feline leukemia virus. Methods of generating retrovirus and lentivirus vectors and their uses have been well described in the art (see, for example, U.S. Pat. Nos. 7,211,247; 6,979,568; 7,198,784; 6,783,977; and 4,980,289).

Suitable herpesvirus vectors can be derived from any one of a number of different types of herpesviruses, including, but not limited to, herpes simplex virus-1 (HSV-1), HSV-2 and herpesvirus saimiri. Recombinant herpesvirus vectors, their construction and uses are well described in the art (see, for example, U.S. Pat. Nos. 6,951,753; 6,379,6741 6,613,892; 6,692,955; 6,344,445; 6,319,703; and 6,261,552; and U.S. Patent Application Publication No. 2003-0083289).

One skilled in the art can readily determine an effective amount of a miR gene product to be administered to a given subject, by taking into account factors, such as the size and weight of the subject; the extent of disease progression; the age, health and sex of the subject; the route of administration; and whether the administration is regional or systemic.

For example, an effective amount of an isolated miR gene product can be based on the approximate body weight of a subject to be treated. Such effective amounts can be administered by any suitable route, such as, for example, intravenous or intraarterial. In some examples, an effective amount of the isolated miR gene product that is administered to a subject can range from about 5 to about 3000 micrograms/kg of body weight, from about 700 to about 1000 micrograms/kg of body weight, or greater than about 1000 micrograms/kg of body weight.

One skilled in the art can also readily determine an appropriate dosage regimen for the administration of an isolated miR gene product to a given subject. For example, a miR gene product can be administered to the subject once (e.g., as a single injection or deposition). Alternatively, a miR gene product can be administered once or twice daily to a subject for a period of from about three to about twenty-eight days, more particularly from about seven to about ten days. In a particular dosage regimen, a miR gene product is administered once a day for seven days. Where a dosage regimen comprises multiple administrations, it is understood that the effective amount of the miR gene product administered to the subject can comprise the total amount of gene product administered over the entire dosage regimen.

Agents can be administered to a subject in need of treatment using any suitable means known in the art. Methods of administration include, but are not limited to, intraductal, intradermal, intramuscular, intraperitoneal, parenteral, intravenous, subcutaneous, vaginal, rectal, intranasal, inhalation, oral or by gene gun. Intranasal administration refers to delivery of the compositions into the nose and nasal passages through one or both of the nares and can comprise delivery by a spraying mechanism or droplet mechanism, or through aerosolization of the nucleic acid or virus. Administration of the compositions by inhalant can be through the nose or mouth via delivery by spraying or droplet mechanisms. Delivery can be directly to any area of the respiratory system via intubation. Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local.

Agents can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers dextrose, dextrose and sodium chloride, lactated Ringers, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose required will vary from subject to subject depending on the species, age, weight and general condition of the subject, the particular therapeutic agent being used and its mode of administration. An appropriate dose can be determined by one of ordinary skill in the art using only routine experimentation.

In some embodiments, the therapeutic agent is a nucleic acid molecule, such as a miR gene product, a vector encoding a miR gene product, an antisense compound or a vector encoding an antisense compound. A nucleic acid-based therapeutic agent can be administered to a subject by any suitable route. In some examples, the agents are administered using an enteral or parenteral administration route. Suitable enteral administration routes include, for example, oral, rectal, or intranasal delivery. Suitable parenteral administration routes include, for example, intravascular administration (such as intravenous bolus injection, intravenous infusion, intra-arterial bolus injection, intra-arterial infusion and catheter instillation into the vasculature); subcutaneous injection or deposition, including subcutaneous infusion (such as by osmotic pumps); direct application to the tissue of interest, for example by a catheter or other placement device (e.g., a suppository or an implant comprising a porous, non-porous, or gelatinous material); and inhalation. Particularly suitable administration routes are injection, infusion and direct injection into a target tissue.

In the context of the present disclosure, a miR gene product or an antisense compound can be administered to the subject either as naked RNA or DNA in combination with a delivery reagent, or can be encoded by a recombinant plasmid or viral vector. Recombinant plasmids and viral vectors including sequences that express the miR gene products or antisense compounds, and techniques for delivering such plasmids and vectors to target cells, are well known in the art.

In some embodiments, liposomes are used to deliver a miR gene product or antisense compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of several factors, such as the desired liposome size and half-life of the liposomes in the blood stream. A variety of methods are known in the art for preparing liposomes (see, for example, Szoka et al., Ann. Rev. Biophys. Bioeng. 9:467, 1980; and U.S. Pat. Nos. 4,235,871; 4,501,728; 4,837,028; and 5,019,369). In some embodiments, polymers can be used to deliver a miR gene product or antisense compound to a subject. Cationic lipids and polymers that can be used to deliver therapeutic RNA molecules have been described (see, for example, Zhang et al., J Control Release. 123(1):1-10, 2007; Vorhies et al., Methods Mol Biol. 480:11-29, 2009; and U.S. Patent Application Publication No. 2009/0306194). Polypeptide carriers can also be used to administer a miR gene product to a subject (see, for example, Rahbek et al., J. Gene Med. 10:81-93, 2008).

Appropriate doses of small molecule agents depend upon a number of factors known to those or ordinary skill in the art, e.g., a physician. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

Also disclosed is a method of determining the effectiveness of an agent for treating and/or preventing arterial plaque rupture or an associated inflammation response in a subject. The method including detecting expression of at least one of miR-221, miR-222, and circR-284 in a sample obtained from the subject following treatment with the agent and comparing expression of the at least one of miR-221, miR-222, and circR-284 in a sample obtained from the subject following treatment to a reference value, wherein an alteration in the expression of the at least one of miR-221, miR-222, and circR-284 following treatment indicates that the agent is effective for the agent for treating and/or preventing arterial plaque rupture or an associated inflammation response in the subject. In some embodiments, the reference value represents an expression value of the at least one of miR-221, miR-222, and circR-284 in a sample from the subject prior to treatment with the agent.

Example

This example describes the determination of the ability of specific microRNAs (miRs) and circular RNAs (circRs) to serve as diagnostic biomarkers of carotid-related ischemic stroke.

Early detection of acute ischemic stroke has the potential to reduce morbidity and mortality in subjects with advanced carotid artery disease (Saver et al., JAMA. 2013; 309:2480-2488). Stable plaques are characterized by a necrotic core with an overlying fibrous cap composed of vascular smooth muscle cells (VSMCs) in a collagen rich matrix (Libby, *N Engl J Med.* 2013; 368:2004-2013). In vulnerable plaques, the fibrous cap is thinner, exhibiting fewer VSMCs and increased inflammatory cells. Therefore, as disclosed herein a strategy for developing diagnostics of a carotid related ischemic cerebrovascular event is identifying circulating biomarkers of fibrous cap thinning.

It has been previously reported by the inventors that microRNA (miR)-221 and -222, but not miR-145, were reduced in the shoulders of carotid plaques following an acute ischemic cerebral event (Bazan et al., *Stroke.* 2015; 46:3285-3287). miR-221 and -222 promote intimal thickening through down-regulation of $p27^{Kip1}$, a cyclin dependent kinase inhibitor that inhibits VSMC cell cycle progression (Liu et al., *J Mol Cell Cardiol.* 2012; 52:645-655; Liu et al., *Circ Res.* 2009; 104:476-487). miR-145 inhibits intimal thickening through promotion of VSMC differentiation (Cheng et al., *Circ Res.* 2009; 105:158-166). Recently, a large number of a second form of non-coding RNA (ncRNA), circular RNAs (circR), was discovered including circR-284 (circbase.org) (Memczak et al., *Nature.* 2013;

495:333-338), which was found to possess a miR-221 and -222 binding site and may serve to regulate miR-221/222 activity.

As disclosed herein, as a corollary to the recent findings in the carotid plaque, the inventors have found that serum miR-221 levels are reduced following plaque rupture. Furthermore, circR-284 is expressed in the carotid plaque and is increased in the sera of subjects following plaque rupture. This discovery demonstrates that the ratio of circR-284 to miR-221 in serum serves as a diagnostic biomarker for carotid related cerebrovascular ischemia.

Methods

Serum levels of miR-145, -221, -222, and circR-284 were measured in 24 subjects without a previous cerebrovascular event in the previous 6 months (Asymptomatic) and 17 subjects with either an acute stroke or transient ischemic attack within the past 5 days (Urgent) while undergoing carotid endarterectomy (CEA) using real-time PCR with the primers listed in Table 2. There were no significant differences in age, gender, smoking status, body mass index (BMI), lipid panel, or serum creatinine between the Asymptomatic and Urgent CEA groups (Table 3).

Subject Population

Serum was collected from 41 non-diabetic subjects undergoing carotid endarterectomy (CEA). Subjects were stratified into two groups, those without a previous cerebrovascular event in the previous 6 months (asymptomatic) and those with either an acute stroke or transient ischemic attack within 5 days of the CEA (urgent).

RNA Isolation and Analysis

Total RNA was isolated from the serum using the miRNeasy® Serum/Plasma kit (Qiagen® Inc., Valencia, Calif.) with minor modifications. miRs were measured using the miScript II RT Kit coupled with the miScript SYBR® Green PCR Kit (Qiagen®). The catalog numbers for the individual miR PCR assays are listed in Table 2. Convergent and divergent primers were used to confirm expression and compare serum levels of circR-284 (Memczak, et al., Nature. 2013; 495:333-338). Relative expression was calculated by the $2^{-\Delta\Delta Ct}$ method. The ratio of circR-284:miR-221 was calculated as $2^{-(\Delta\Delta Ct)}$ with $\Delta C_t = C_{t(miR-221)} - C_{t(circR-284)}$ and $\Delta\Delta C_t = \Delta C_{t(urgent)} - \Delta C_{t(asymptomatic)}$.

Statistics

Data is expressed as the mean+/−standard error of the mean. Statistical analysis between groups was performed using Student's t-test. $X^2$ analysis was used to compare categorical variables across groups. All analyses were performed using SPSS v19.0 (IBM).

Results

Figure 5A:
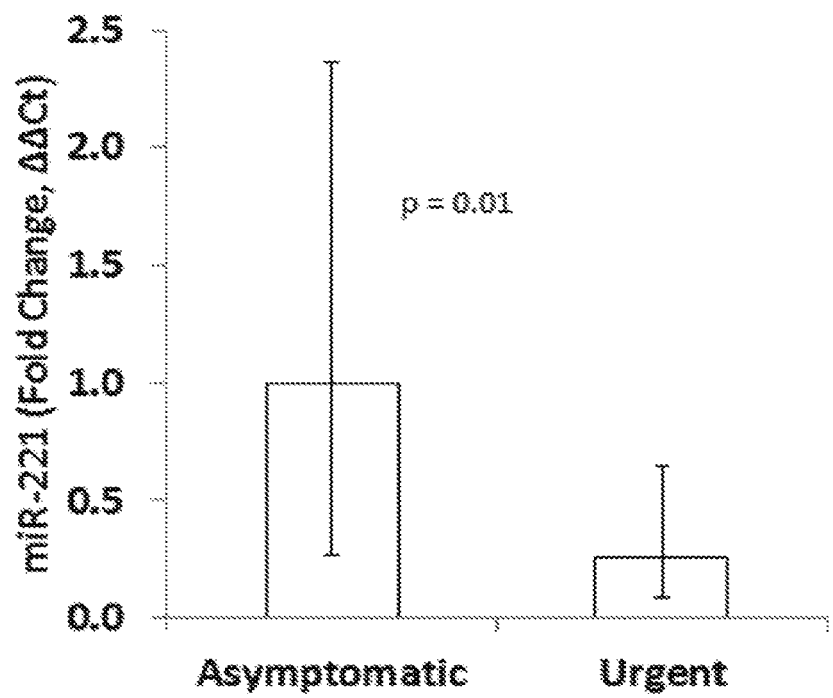
FIG. 5A is a bar graph of serum levels of miR-221, showing the quantification of miR-221 in the serum of Asymptomatic and Urgent subjects.
Figure 5B:
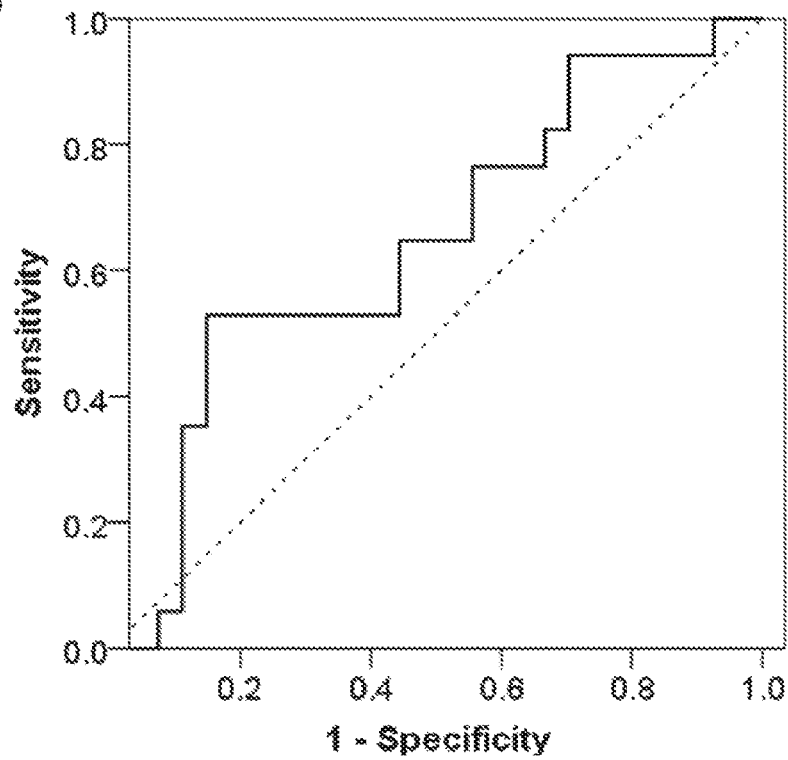
FIG. 5B is a graph of receiver operating characteristic (ROC) analysis of miR-221 (solid line) as an indicator of a recent ischemic cerebrovascular event. The dashed line is the line of no-discrimination.

It was recently reported that miR-221 and -222 are reduced in the carotid plaque shoulder of subjects immediately following an acute cerebrovascular event (Bazan et al., Stroke. 2015; 46:3285-3287). To determine if these changes were reflected in the serum, miR-221, -222, and -145 circulating levels were compared in the Asymptomatic and Urgent groups. Similar to a report by Tsai et al. (Tsai et al., J Vasc Res. 2013; 50:346-354), miR-145 and additionally miR-222 were not detectable in a majority of the samples. The Urgent group exhibited a significantly lower level of miR-221 than the Asymptomatic group (0.25±0.11 vs. 1.00±0.31, p=0.01, FIG. 5A). Receiver operator curve (ROC) analysis suggested miR-221 levels alone do not sufficiently discriminate between the Asymptomatic and Urgent groups to serve as a good predictor of plaque rupture (e.g. Urgent status, FIG. 5B).

Figure 6A:
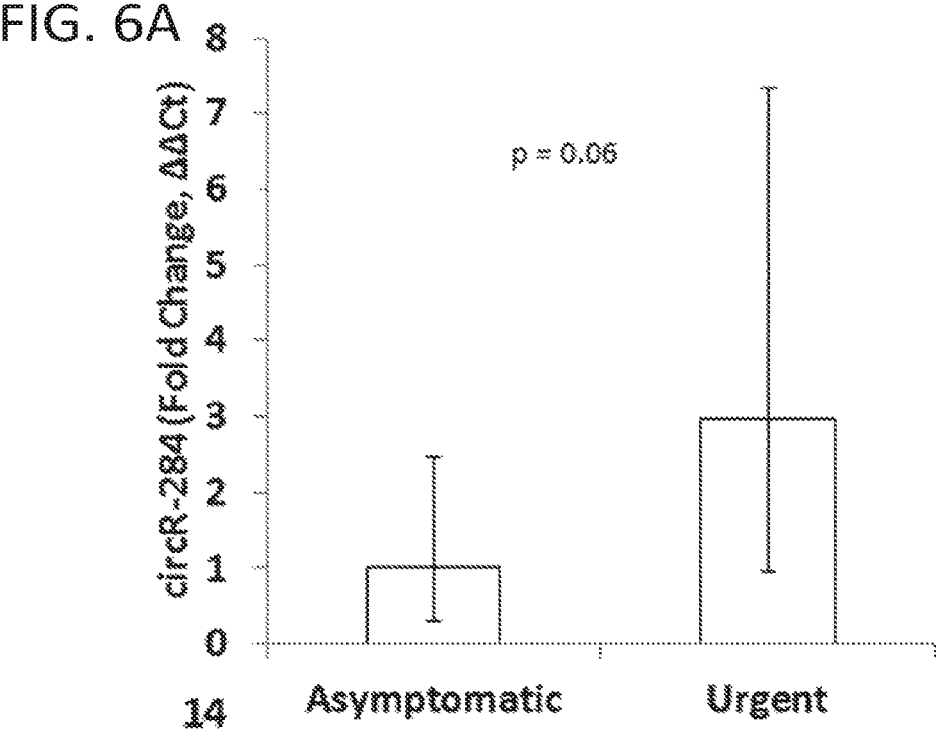
FIG. 6A is a bar graph of serum levels of circR-284 showing quantification of circR-284 in the serum of Asymptomatic and Urgent subjects.
Figure 6B:
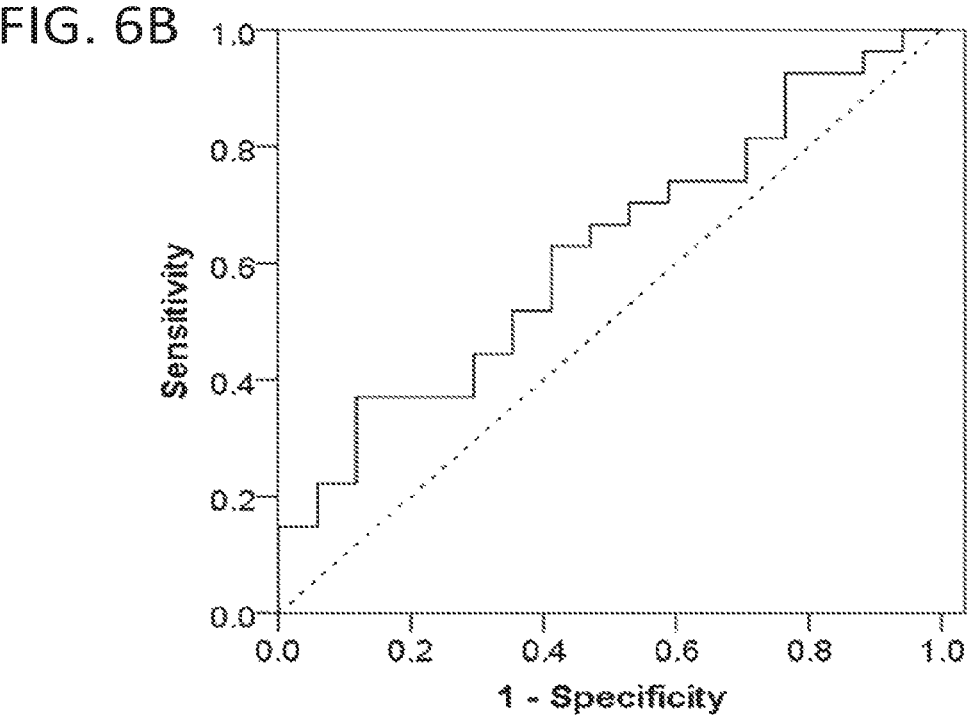
FIG. 6B is a graph of ROC analysis of circR-284 (solid line) as an indicator of a recent ischemic cerebrovascular event. Dashed lines are the lines of no-discrimination.

As circR-284 has a potential miR-221 binding site, trials were conducted to determine whether it is expressed in VSMCs. It was confirmed that circR-284 is expressed in human VSMCs (FIG. 6A) and in carotid plaques (data not shown). In contrast to miR-221, serum circR-284 levels exhibit an increase following an acute carotid plaque rupture-mediated cerebral ischemic event (2.96±1.16 vs. 1.00±0.37, p=0.06, FIG. 6A). Again, ROC analysis suggests that serum circR-284 alone is a poor diagnostic for plaque rupture (FIG. 6B).

Figure 6C:
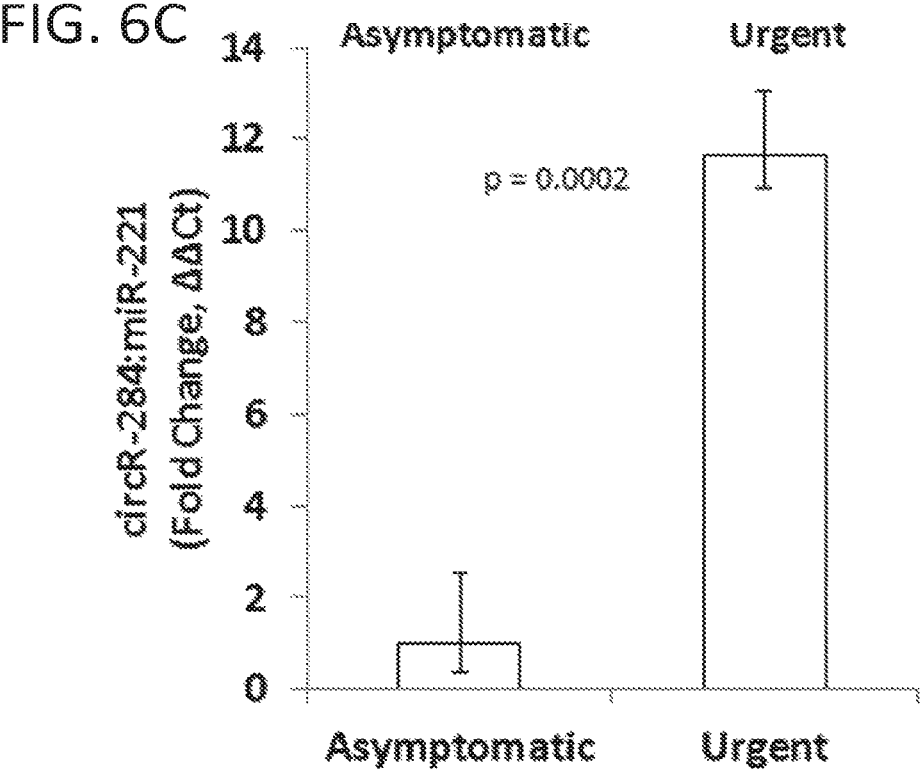
FIG. 6C is a bar graph of serum showing the ratio of circR-284:miR-221 in the serum of Asymptomatic and Urgent subjects.
Figure 6D:
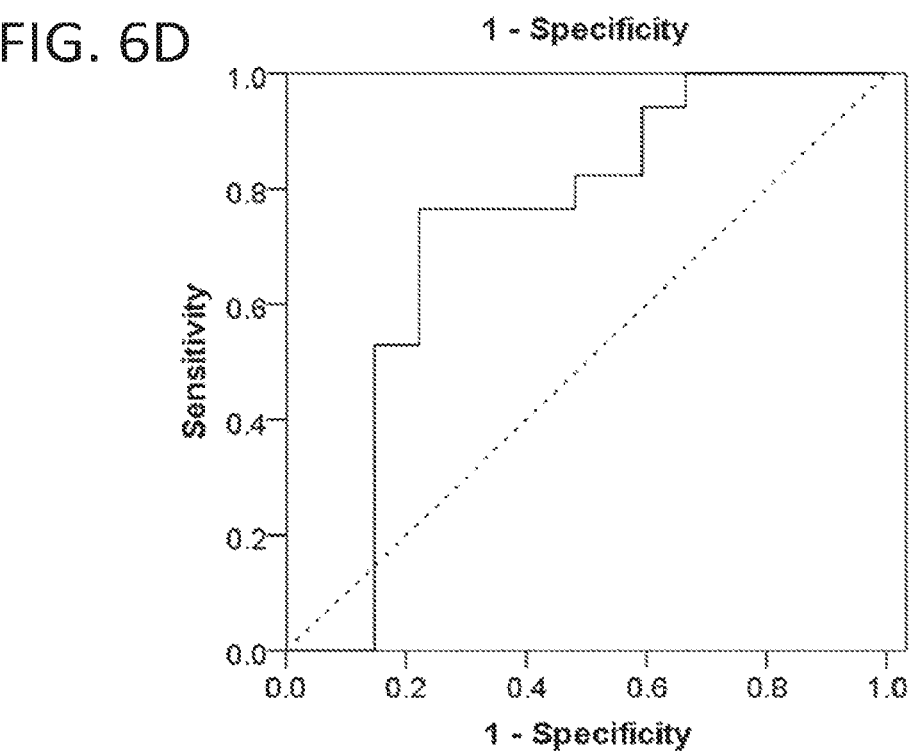
FIG. 6D is a graph of ROC analysis of the ratio of circR-284:miR-221 (solid line) as an indicator of a recent ischemic cerebrovascular event. Dashed lines are the lines of no-discrimination.

Given the inverse relationship between miR-221 and circR-284, it was tested whether the ratio of circR-284 to miR-221 would yield a serum biomarker of a carotid related cerebrovascular ischemic event. It was found that the ratio of circR-284 to miR-221 was significantly higher in the Urgent group compared to the Asymptomatic group (11.7±0.48 vs. 1.0±0.6, p=0.0002, FIG. 6C). There were no significant differences in the ratio of serum circR-284 to miR-221 with respect to gender, history of smoking, statin use, race, presence of chronic kidney disease nor was there a significant correlation between the serum ncRNAs levels and age, BMI, lipid panel, or serum creatinine (Tables 4 and 5). Comparison of the sensitivity, specificity, likelihood ratios, accuracy, and ROCs of the miR-221 and circR-284: miR-221 tests demonstrate that the circ-284:miR-221 ratio can be used as a diagnostic test for an acute ischemic cerebrovascular event following carotid plaque rupture (FIG. 6D and Table 1).

Discussion

It was recently reported by the inventors that miR-221 and -222 expression in the carotid plaque shoulder is reduced immediately following a carotid related ischemic cerebrovascular event and returns to normal levels after seven days (Bazan et al., Stroke. 2015; 46:3285-3287). It is disclosed herein that serum levels of miR-221 are decreased following an ischemic cerebrovascular event comparable to that observed in carotid tissue. This decrease was greater than that reported by Tsai et al. perhaps due to the shorter time between event and sample collection in our cohort compared to theirs (2.6 vs. ~7 days).

Normalization of serum measurements of individual ncRNAs is difficult as the standard housekeeping genes are not reliable in serum (Benz et al., Exp Mol Med. 2013; 45:e42). The use of a spike-in control did not enhance the data (data not shown). It was therefore tested whether a potential functionally-related ncRNA could, in combination with miR-221, serve as a biomarker of carotid plaque rupture. While serum circR-284 alone does not appear promising as a biomarker, the ratio of circR-284 to miR-221 is significantly increased following plaque rupture and exhibits sensitivity and specificity that demonstrates that ability to discriminate between the Asymptomatic and Urgent subjects. Beyond this clinical setting, pairs of functionally-related ncRNAs as circulating biomarkers may yield more accurate biomarkers than standard normalization methods.

TABLE 1

Evaluation of Biomarkers

| Marker | Value | AUC 95% CI | p-value | Sensitivity | Specificity | LR+ | LR− | Accuracy, % |
|---|---|---|---|---|---|---|---|---|
| miR-221 | .721 | 0.554-0.887 | .017 | 0.588 | 0.625 | 1.569 | 0.659 | 61% |
| circR-284 | .654 | 0.486-0.823 | .095 | 0.529 | 0.667 | 1.588 | 0.706 | 61% |

TABLE 1-continued

Evaluation of Biomarkers

| Marker | AUC Value | 95% CI | p-value | Sensitivity | Specificity | LR+ | LR− | Accuracy, % |
|---|---|---|---|---|---|---|---|---|
| circR-284:miR-221 | .824 | 0.69-0.957 | .000 | 0.765 | 0.875 | 6.118 | 0.269 | 83% |

LR+ Likelihood ratio positive, LR− Likelihood ratio negative

TABLE 2

Primer Assays

| Name | Qiagen Cat # |
|---|---|
| miR221 | ms00003857 |
| MiR222 | ms00007609 |
| MiR145 | ms00003528 |

TABLE 3

Characteristics of Subjects

| Characteristics | Total (n = 41) | Asymptomatic (n = 24) | Urgent (n = 17) | P-value |
|---|---|---|---|---|
| Age, y | 68.4 ± 1.9 | 69.1 ± 2.4 | 67.5 ± 3.2 | 0.68 |
| Male Sex | 30 (73) | 16 (67) | 14 (82) | 0.20 |
| Body Mass Index, lb/in2 | 27.1 ± 0.9 | 27.0 ± 1.3 | 27.1 ± 1.2 | 0.99 |
| Total Cholesterol, mg/dL | 158.7 ± 9.0 | 152.9 ± 14.1 | 162.8 ± 12.0 | 0.60 |
| HDL, mg/dL | 44.4 ± 2.0 | 45.3 ± 3.8 | 43.7 ± 2.2 | 0.70 |
| LDL, mg/dL | 93.6 ± 5.3 | 86.2 ± 10.0 | 98.9 ± 5.5 | 0.28 |
| Triglycerides, mg/dL | 118.3 ± 11.0 | 107.1 ± 14.8 | 126.2 ± 15.7 | 0.38 |
| Serum Creatinine, mg/dL | 1.1 ± 0.1 | 1.0 ± 0.1 | 1.1 ± 0.1 | 0.52 |
| Smoker | 9 (22) | 5 (21) | 4 (24) | 0.71 |
| Time to CEA, days | | | 2.6 ± 0.3 | |

TABLE 4

Fold Change in Categorical Variables

| Group | Fold Change | 95% CI | p-value |
|---|---|---|---|
| Male | 1.97 | 0.40-9.72 | 0.40 |
| Smoker | 2.37 | 0.49-11.61 | 0.28 |
| African American | 0.91 | 0.06-14.07 | 0.94 |
| Statin Use | 0.58 | 0.13-2.65 | 0.47 |
| Chronic Kidney Disease | 1.40 | 0.21-9.34 | 0.72 |

TABLE 5

Correlation between serum circR-284:miR-221 and continuous variables

| Variable | R | p-value |
|---|---|---|
| Total Cholesterol | −.132 | .496 |
| High Densityy Lipoprotein | −.088 | .650 |
| Low Density Lipoprotein | −.135 | .484 |
| Triglycerides | −.111 | .565 |
| Serum Creatinine | .144 | .369 |
| Age | .194 | .224 |
| Body Mass Index | .065 | .685 |

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method comprising:
   detecting expression of at least one of micro RNA-221 (miR-221) and miR-222 in a sample obtained from a subject with or believed to have an arterial plaque rupture in an artery;
   detecting expression of circular RNA-284 (circR-284) in the sample obtained from the subject;
   detecting a ratio of expression levels of circR-284 to at least one of miR-221 and miR-222 greater than a reference value indicative of a no rupture indicating that the subject has experienced arterial plaque rupture; and
   administering an effective amount of tissue plasminogen activator (tPA) to the subject having the detected ratio of expression levels greater than the reference value.

2. The method of claim 1, further comprising, selecting a subject with, or believed to have, suffered a stroke and/or transient ischemic attack (TIA) or a myocardial infarction.

3. The method of claim 1, wherein the method is used for diagnosing or prognosis of a subject with stroke and/or myocardial infarction.

4. The method of claim 1, wherein the expression of miR-221, miR-222, and/or circR-284 is detected with a probe and/or primers that respectively specifically bind to miR-221, miR-222, and/or circR-284, or an amplification product thereof, wherein the probe and/or primers are labeled with a detectable label.

5. A method of treating a stroke or myocardial infarction in a subject, comprising:
- detecting expression of at least one of micro RNA-221 (miR-221) and miR-222 in a sample from a subject suffering from or believed to have experienced a stroke or myocardial infarction;
- detecting expression of circular RNA-284 (circR-284) in a sample obtained from the subject; and
- detecting a ratio of expression levels of circR-284 to at least one of miR-221 and miR-222 greater than a reference value indicating that the subject would benefit from treatment with tissue plasminogen activator (tPA); and
- administering to the subject having the detected ratio of expression levels greater than the reference value an effective amount of tPA, thereby treating the stroke or myocardial infarction in the subject.

6. The method of claim 5, further comprising, selecting a subject with, or believed to have, suffered a stroke and/or transient ischemic attack (TIA) or a myocardial infarction.

7. The method of claim 5, further comprising, comparing the expression of one or more of miR-221, miR-222, or circR-284 to a control.

8. The method of claim 5, wherein the expression of miR-221, miR-222, and/or circR-284 and/or is detected with a probe and/or primers that specifically bind to miR-221, miR-222, and/or circR-284 and/or, or an amplification product thereof wherein the probe and/or primers are labeled with a detectable label.

* * * * *